US011169670B2

(12) United States Patent
Krimsky et al.

(10) Patent No.: US 11,169,670 B2
(45) Date of Patent: Nov. 9, 2021

(54) REMOTE MEDICAL EVALUATION HEURISTIC

(71) Applicants: William Sanford Krimsky, Forest Hill, MD (US); Robyn Mi Jung Baek, Falls Church, VA (US); Hai Viet Tran, Vienna, VA (US)

(72) Inventors: William Sanford Krimsky, Forest Hill, MD (US); Robyn Mi Jung Baek, Falls Church, VA (US); Hai Viet Tran, Vienna, VA (US)

(*) Notice: Subject to any disclaimer, the term of this patent is extended or adjusted under 35 U.S.C. 154(b) by 324 days.

(21) Appl. No.: 16/525,241

(22) Filed: Jul. 29, 2019

(65) Prior Publication Data

US 2020/0026401 A1 Jan. 23, 2020

Related U.S. Application Data

(63) Continuation-in-part of application No. 14/814,254, filed on Jul. 30, 2015, now Pat. No. 10,417,383.
(60) Provisional application No. 62/703,931, filed on Jul. 27, 2018, provisional application No. 62/031,714, filed on Jul. 31, 2014.

(51) Int. Cl.
*G06F 3/0484* (2013.01)
*A61B 5/00* (2006.01)
*G16H 50/70* (2018.01)
*G16H 10/60* (2018.01)

(52) U.S. Cl.
CPC .......... *G06F 3/0484* (2013.01); *A61B 5/0022* (2013.01); *A61B 5/7275* (2013.01); *A61B 5/742* (2013.01); *G16H 10/60* (2018.01); *G16H 50/70* (2018.01)

(58) Field of Classification Search
CPC ...... G06F 3/0484; G16H 10/60; G16H 50/70; A61B 5/0022; A61B 5/7275; A61B 5/742
USPC .......................................................... 705/2
See application file for complete search history.

(56) References Cited

U.S. PATENT DOCUMENTS

| 10,270,865 B1* | 4/2019 | Heath ................. H04M 3/5191 |
| 2008/0140160 A1* | 6/2008 | Goetz ................ A61N 1/37288 607/60 |
| 2013/0060576 A1* | 3/2013 | Hamm ................... G16H 40/67 705/2 |
| 2014/0095592 A1* | 4/2014 | Hartrick ............... H04L 47/767 709/203 |
| 2014/0207477 A1* | 7/2014 | Forthman ........ G06Q 10/06393 705/2 |

(Continued)

*Primary Examiner* — Michael Tomaszewski
(74) *Attorney, Agent, or Firm* — Royal W. Craig; Gordon Feinblatt LLC

(57) ABSTRACT

A system can establish, handoff, and monitor the integrity of a remote network connection between a health care professional and a health care facility. The system can update treatment status indicators and treatment compliance indicators for the facility based on data received from a health care assessment of a patient at the facility conducted over the remote network connection. The system can calculate a care score based on the updated treated status indicators and calculate a facility score based on the care score and updated treatment compliance data. The system can determine patient care risk for the facility and predict treatment outcomes for patients based on the calculated facility score. The system can provide indicators of the patient care risk and predicted patient outcome to the facility via a user-interface.

20 Claims, 22 Drawing Sheets

(56) References Cited

U.S. PATENT DOCUMENTS

2014/0278550 A1* 9/2014 Pestka .................... G16Z 99/00
                                                      705/3
2016/0065450 A1* 3/2016 McAllister .......... H04L 12/4625
                                                      370/218

* cited by examiner

CRITICAL CARE SMART SHEET     400

1. General orienting sentence on the patient (e.g. 62 yo man admitted for pneumonia):

2. Identify Chief Physiologic Deterioration (See FIG. 4B)

3. Process Metrics Evaluation:
   a. Are there any devices in place (lines, tubes, etc.)? Y/N
      • If YES - are any or all of them still necessary Y/N
   b. Has this patient reached their nutritional goal? Y/N
      • If NO - has this been addressed with patient's attending? Y/N
   c. Are there current issues with pain management in this patient? Y/N
      • If YES - have these been addressed? Y/N
   d. Is skin integrity intact? Y/N
      • If NO - is this being addressed? Y/N
   e. Are there issues with delirium? Y/N
      • If YES - are these being addressed? Y/N
   f. Is this patient on appropriate prophylaxis (VTE, SUP, VAP, etc.)? Y/N
      • If NO - are these being addressed Y/N
   g. Has the patient been mobilized Y/N
   h. Are there ethical or care philosophy or family issues Y/N 4. Do you or your patient need help? -- If yes, then SOC SMART Doctor will coordinate a consult for the patient.

FIG. 4A not all inclus

• A step change in systolic BP by 40 mm
• A systolic BP < 90 mm
• A MAP < 60 mm
• Heart rate of 120 or greater
• An abrupt change in mental status
• A change in perfusion (i.e. decreased UO, mottling, escalating lactate)
• An increase in FiO2 required by 30%
• An increase in RR to 28 or greater

FIG. 4B

SMART Sign-out

Patient Name: _____ DOB: _____

Hospital: _____

City, State: _____

1. General orienting sentence on the patient (e.g., 62 yo man admitted for phneumonia):

2. Identify Chief Physiologic Deterioration (see below)

3. Process Metrics Evaluation:
   a. Are there any devices in place (lines, tubes, etc.)?  Yes   No b. Has this patient reached their nutritional goal?  Yes   No c. Are there current issues with pain management in this patient?  Yes   No d. Is skin integrity intact?  Yes   No e. Are there issues with delirium?  Yes   No f. Is this patient on appropriate prophylaxis (VTE, SUP, VAP, etc.)?  Yes   No g. Has the patient been mobilized  Yes   No h. Are there ethical or care philosophy or family issues  Yes   No

4. List the key/critical issues

5. Status change in the past 24 hours?                Yes         No

| Physiological Deterioration (note not all inclusive) | |
|---|---|
| A step change in systolic BP by 40 mm | An abrupt change in metal status |
| A systolic BP < 90 mm | A change in perfusion (i.e. decreased UO, mottling, escalating lactate) |
| A MAP < 60 mm | An increase in FiO2 required by 30% |
| Heart rate of 120 or greater | An increase in RR to 26 or greater |

FIG. 9

REMOTE MEDICAL EVALUATION HEURISTIC

CROSS-REFERENCE TO RELATED APPLICATION(S)

This application claims priority to U.S. provisional patent application 62/703,931, filed 27 Jul. 2018, and is a continuation-in-part of U.S. patent application Ser. No. 14/814,254, filed 30 Jul. 2015, which claims priority to U.S. provisional patent application 62/031,714, filed on 31 Jul. 2014.

BACKGROUND OF THE INVENTION

1. Field of the Invention

The present invention relates generally to health care analytics and, more particularly, to a remote medical evaluation platform, heuristic analysis based thereon, and user dashboard for displaying the analytics that provides institutional filters.

2. Description of the Background

People typically receive health care from multiple providers at multiple locations, and many providers are now using telemedicine to provide clinical health care from a distance. Typically, the patient and the physician are located remotely during the gathering of information. Telemedicine is considered of particular advantage in situations where patients are inaccessible because it eliminates distance barriers, especially in critical care and emergency situations.

Telemedicine entails electronic consultations, e.g., real-time interactions between patient and provider, facilitated through interactive video/audio networks. For example, Applicant's co-pending U.S. patent application Ser. No. 14/814,254 filed 30 Jul. 2015 describes a system and method for triage evaluations for patients in intensive care units ("ICUs") or other clinical areas. A remote evaluation session includes performing an assessment for each patient in an ICU by a remote doctor or other health care professional and generating records related to the assessments. The remote evaluation may include regular (e.g., daily) patient assessment coordinated between remote and on-site personnel.

It can be more difficult to deliver optimum care using a distributed model that includes telemedicine because coordination of care is a challenge. Health care analytical systems are being developed to improve care coordination. However, managing integrity of care requires collection of distributed data plus a complex heuristic analysis. Health care providers commonly lack accurate and up-to-date information regarding the care previously received by a patient from other providers. In order to deliver optimum, coordinated health care and most cost-effective health care to their patients, health care providers need to consolidate all encounter data in the entire chain of care to ensure ready access to an up to date medical history wherever patients receive care. Health care providers need to combine this consolidated encounter data with an ability to analyze a broad array of clinical data, treatment data, and demographics. This analysis needs to be used to optimize care delivery, proactively identify patients in need, assess the ongoing integrity of care, ensure process integrity, and assess common failure modes with respect every patient.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIGS. 4A and 4B are an example of a data sheet (both sides) according to an embodiment of the invention.

FIG. 9 is an example of a sign-out sheet according to an embodiment of the invention.

DETAILED DESCRIPTION OF THE PREFERRED EMBODIMENT

Figure 1:
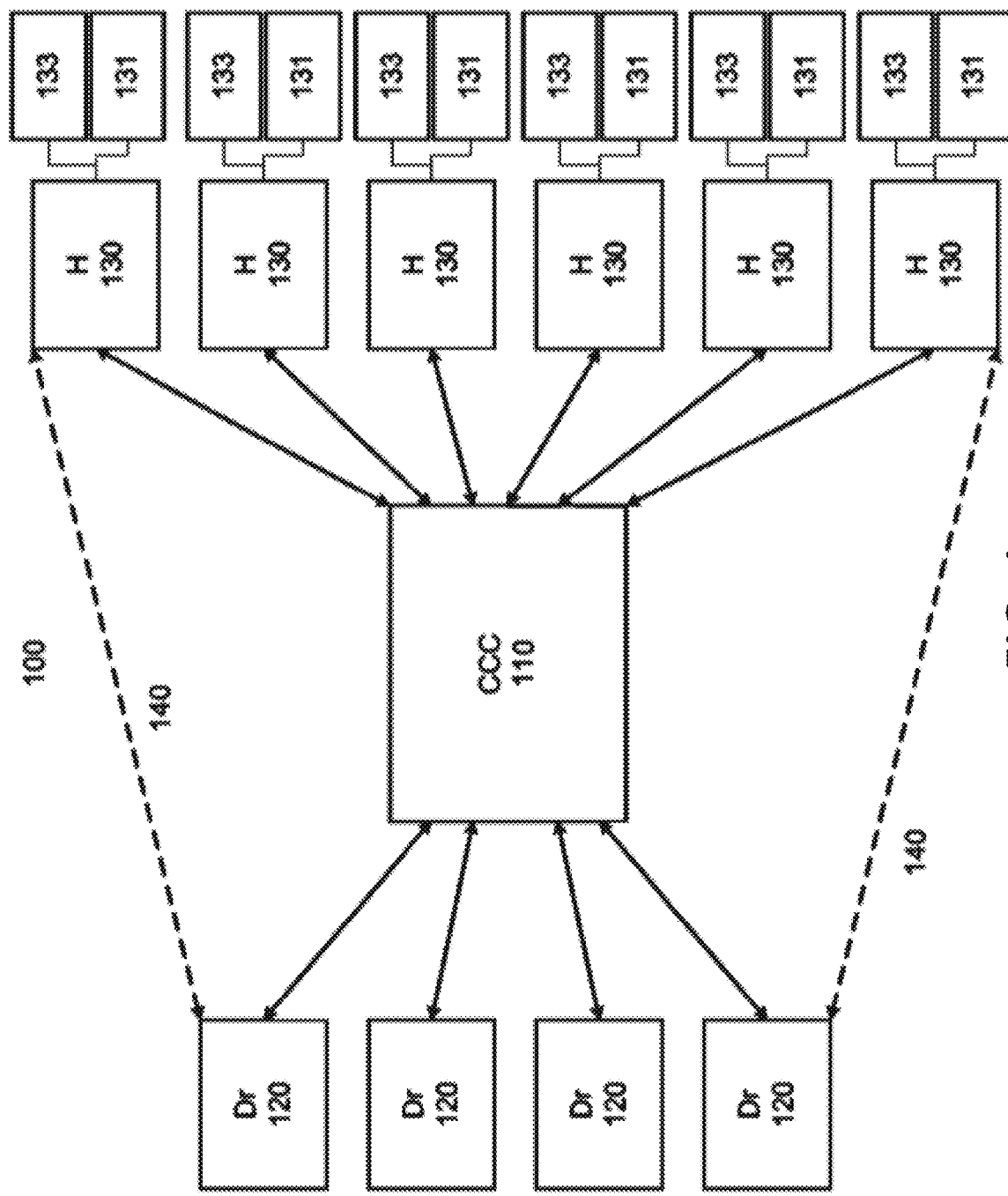
FIG. 1 is a schematic diagram of a network according to an embodiment of the invention.

Reference will now be made in detail to preferred embodiments of the invention, examples of which are illustrated in the accompanying drawings. Wherever possible, the same reference numbers will be used throughout the drawings to refer to the same or like parts.

The present invention includes a system and method for remote medical evaluation of at least one patient in a health care facility by a remote health care professional to determine whether the at least one patient should be given more immediate care. The system can be applied to any acute care medical or surgical unit, using analogous and applicable metrics as defined by patient need and safety.

Embodiments of the invention provide a variety of technological improvements to the technical field of computer networks, including specifically, remote medical evaluation technology. For example, systems according to embodiments of the invention can establish, by a clinical or consult coordination center (CCC) computer, a remote connection between a health care professional's computer and a computer at a health care facility. The system can handoff the remote connection such that data exchanged between the health care professional's computer and facility computer does not pass through the CCC computer. For example, the CCC computer execute procedures in accordance with a connection protocol to establish a network connection to a computer at the health care facility and a health care professional's computer, such that the CCC computer, health care facility computer and/or the health care professional's computer are each connected to the network connection. The CCC computer can then provide an instruction to the health care facility computer and/or the health care professional's computer to execute procedures in accordance with a connection protocol to establish a network connection between the health care facility computer and the health care professional computer, such as a direct connection that does not include the CCC computer.

The system can continue to monitor the integrity of the remote connection after the connection is handed off. This integrity monitoring can allow for reestablishment of the remote connection, if the connection integrity degrades. As a result, the CCC computer can control which computers connect to one another and monitor and reestablish connections between the connected computers, without undertaking the burden of handling the data traffic between the connected computers. For example, after a direct connection is established between the health care facility computer and the health care professional computer, the CCC computer can remain connected to the health care facility computer and/or the health care professional computer and access metadata about the direct connection such as the volume, rate, quality, and/or latency of the direct connection. In some embodiments, such metadata may be provided to the CCC computer by establishing a new connection between the CCC computer and the health care professional computer and/or the health care facility computer rather than maintaining the initial connection. If such metadata indicates the integrity of the direct connection is poor, such as when the network latency is above a threshold level, then the CCC computer, the health care facility computer, and/or the healthcare professional computer can terminate the direct connection, and the direct connection can be reestablished, such as by executing procedures described above regarding the initial establishment of the direct connection. This technical improvement increases the operating efficiency of the CCC computer by reducing its network data traffic load to allow the CCC computer to establish and monitor more connections between external computers than would be possible if the CCC computer was also handling the network data traffic between externally connected computers.

The system may employ a CCC computer, which can include application service provider (ASP) computers in communication with one or more health care provider computers, e.g., doctors and hospitals, although other specialists or facilities may be present in the network. For example, the system may be employed in health care facilities, such as an ambulatory surgery center, an outpatient clinic, a rehabilitation center, a nursing home, an assisted living facility, a patient home, a military medical facility, a skilled nursing facility, and a freestanding emergency center. In some embodiment the system can monitor 500 or more health care facilities.

Systems and methods described herein may provide remote safety management and recommended triage evaluations for patients in intensive care units (ICUs) or other clinical areas. A remote evaluation session may include performing an assessment for each patient in an ICU by a remote doctor or other health care professional (e.g., a surgeon, a medical doctor, a medical scientist, a physical therapist, a behavioral therapist, a physician's assistant, nurse, etc. hereinafter collectively referred to as "doctor"), and generating records related to the assessments. The remote evaluation may proactively identify patients in need and assess the ongoing integrity of care. The remote evaluation may include regular (e.g., daily) patient assessment coordinated between remote and on-site personnel which may enable a brief "eyes-on" daily patient assessment, ensure process integrity, and assess common failure modes with respect to the disciplinary work that should be done on every patient. The remote evaluation may also establish a bi-directional channel to ask for and/or to provide further help. If it is established that further help is required, then the patient may be channeled into a different level of care for a one-to-one evaluation.

Systems and methods described herein may comprise one or more computers, which may also be referred to as processors. A computer may be any programmable machine or machines capable of performing arithmetic and/or logical operations. In some embodiments, computers may comprise processors, memories, data storage devices, and/or other commonly known or novel components. These components may be connected physically or through network or wireless links. Computers may also comprise software which may direct the operations of the aforementioned components. Computers may be referred to with terms that are commonly used by those of ordinary skill in the relevant arts, such as servers, PCs, mobile devices, routers, switches, data centers, distributed computers, and other terms. Computers may facilitate communications between users and/or other computers, may provide databases, may perform analysis and/or transformation of data, and/or perform other functions. It will be understood by those of ordinary skill that those terms used herein are interchangeable, and any computer capable of performing the described functions may be used.

Computers may be linked to one another via a network or networks. A network may be any plurality of completely or partially interconnected computers wherein some or all of the computers are able to communicate with one another. It will be understood by those of ordinary skill that connections between computers may be wired in some cases (e.g., via Ethernet, coaxial, optical, or other wired connection) or may be wireless (e.g., via Wi-Fi, WiMax, or other wireless connection). Connections between computers may use any protocols, including connection oriented protocols such as TCP or connectionless protocols such as UDP. Any connection through which at least two computers may exchange data can be the basis of a network.

Systems and methods described herein also comprise heuristic analytics and a novel intensive care unit telemedicine ("TeleICU") dashboard with the power to revolutionize critical care and deliver better coordinated and more effective care to critically ill patients. The TeleICU allows tele-intensivists using the remote medical evaluation platform to collaborate with the onsite clinical team to develop care plans, provide daily assessments with proactive, structured interactions.

FIG. 1 is a network 100 according to an embodiment of the invention. The network 100 may include a CCC 110 comprising one or more computers in communication with one or more doctor computers 120 and one or more hospitals 130 (e.g., via one or more camera units 131 or other computers 133 at each hospital 130). Doctors and hospitals are shown in this example, although other specialists 120 and facilities 130 may be present in the network 100. For example, the system may be employed in nursing homes, long term acute care facilities and patient homes, among others. The CCC 110 may communicate with doctor computers 120 and hospital 130 computers via any network, such as the Internet. The CCC 110 may also include a call center which may be staffed to handle troubleshooting and/or other calls from doctors and/or hospitals 130. A remote evaluation session may be initiated for a hospital 130, for example at a time scheduled at the CCC 110. The remote evaluation sessions are described in greater detail below, but may generally include remote doctor/patient interaction via a doctor computer 120 and one or more systems at the hospital 130. The CCC 110 may indicate to the one or more doctor computers 120 that the hospital 130 is ready for the remote evaluation session, and a doctor at one of the doctor computers 120 may accept the remote evaluation assignment and begin the remote evaluation session. The CCC 110 may facilitate a direct connection between the doctor computer 120 (and doctor) and the hospital 130 computer. After completion of the remote evaluation session, the hospital 130 or doctor computer 120 may send records generated during the session to the CCC 110, so that they may be used in future sessions. Thus, the CCC 110 may serve as a communications hub for the doctor computers 120 and the hospitals 130 and as a data repository for medical records useful to both the doctors and hospital 130 personnel.

Figure 6:
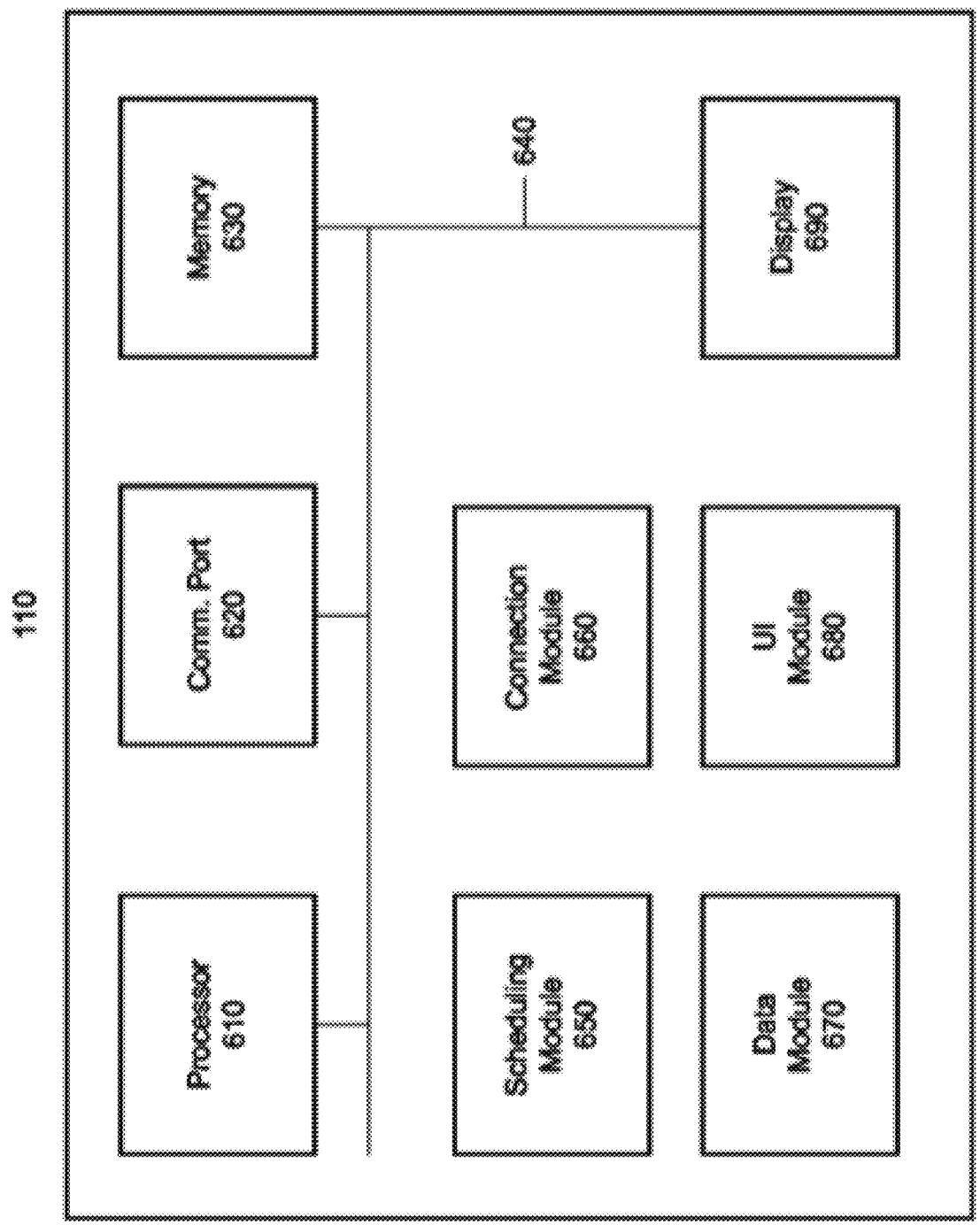
FIG. 6 is a schematic block diagram of a consult coordination center according to an embodiment of the invention.

FIG. 6 is a CCC 110 according to an embodiment of the invention. The CCC 110 may include one or more computers (referred to as "CCC 110 computer"). The one or more computers may include a processor 610, a communication port 620 which may be configured to connect to the network 100, a memory 630, a display 690, and/or other hardware, which may be interconnected by a bus 640. The one or more computers may include a scheduling module 650, a connection module 660, a data module 670, a user-interface (UI) module 680, and/or other modules. Such modules may be software stored in memory 630 and executed on processor 610. Example functions of these modules are described in greater detail below.

FIG. 1 depicts an embodiment of a CCC 110 that is central to a plurality of doctor computers 120 and hospitals 130, but in some embodiments the CCC 110 may be distributed. For example, a geographic region may have several hospitals 130. One of the hospitals 130 in the region may serve as a hub for the remaining hospitals 130 in the region. The hub hospital 130 may include a CCC 110 or elements of a CCC 110. Thus, for example, the hub hospital 130 could perform some or all of the scheduling, communications, data collection, etc. for the regional hospitals 130. The hub hospital 130 may also have remote evaluations performed on its own patients. The hub hospital 130 may include an entire CCC 110, or may be in communication with another CCC 110 as shown in FIG. 1. In some embodiments, CCC 110 may be a clinical care coordination center.

Figure 7:
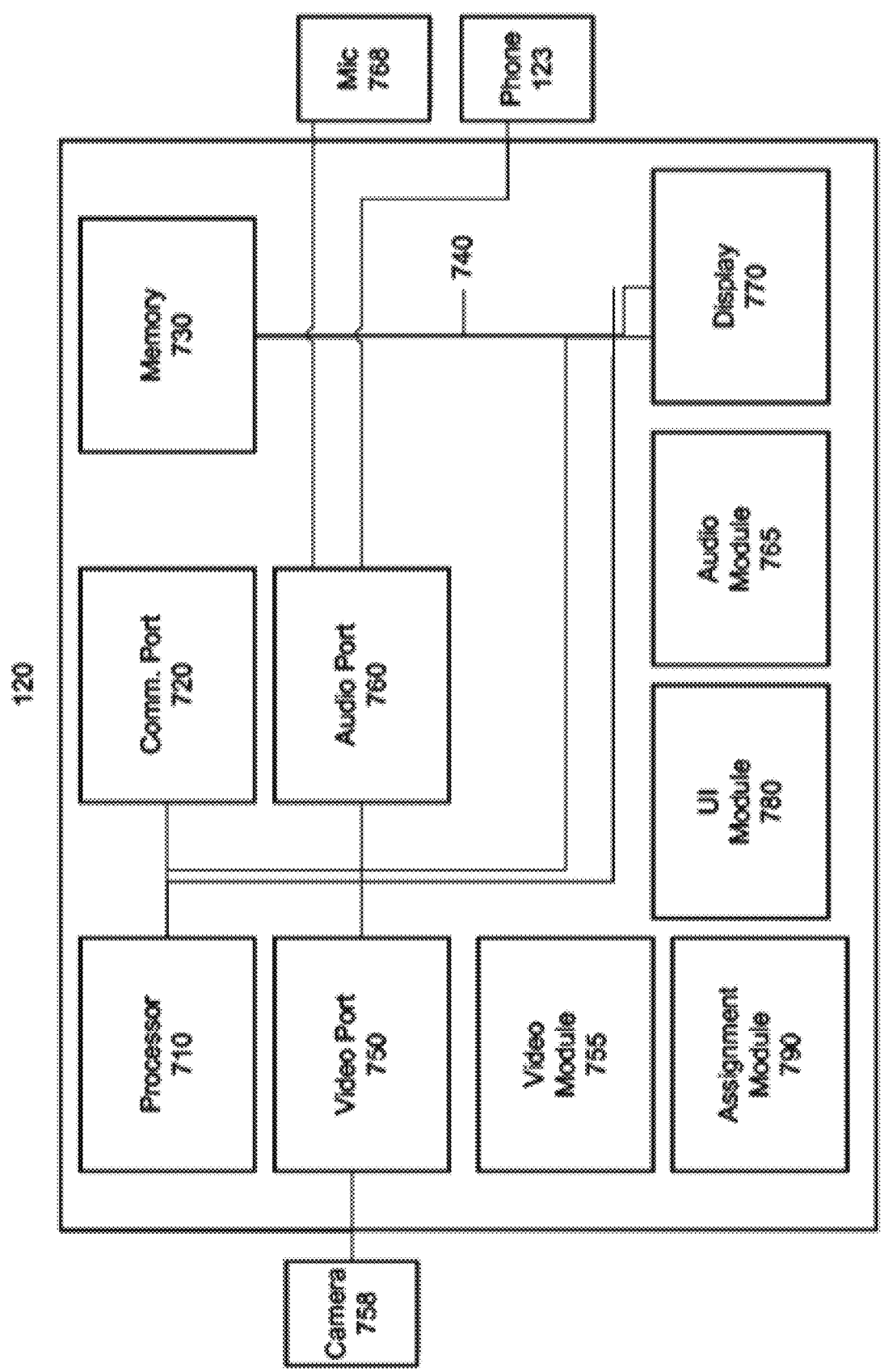
FIG. 7 is a schematic block diagram of a doctor computer according to an embodiment of the invention.

FIG. 7 is a doctor (or health care professional) computer 120 according to an embodiment of the invention. The doctor computer 120 may include one or more computers. The one or more computers may include a processor 710, a communication port 720 which may be configured to connect to the network 100, a memory 730, a video port 750 to which a camera 758 may be connected, an audio port 760 to which a microphone 768 may be connected, a display 770, and/or other hardware, which may be interconnected by a bus 740. The ports may be any ports capable of exchanging data (e.g., Ethernet, USB, etc.). The one or more computers may include a video module 755, an audio module 765, a UI module 780, an assignment module 790, and/or other modules. Such modules may be software stored in memory 730 and executed on processor 710. Example functions of these modules are described in greater detail below. A phone 123 may be part of the doctor computer 120 (e.g., connected via the audio port 760) or may be separate from the doctor computer 120.

Figure 8:
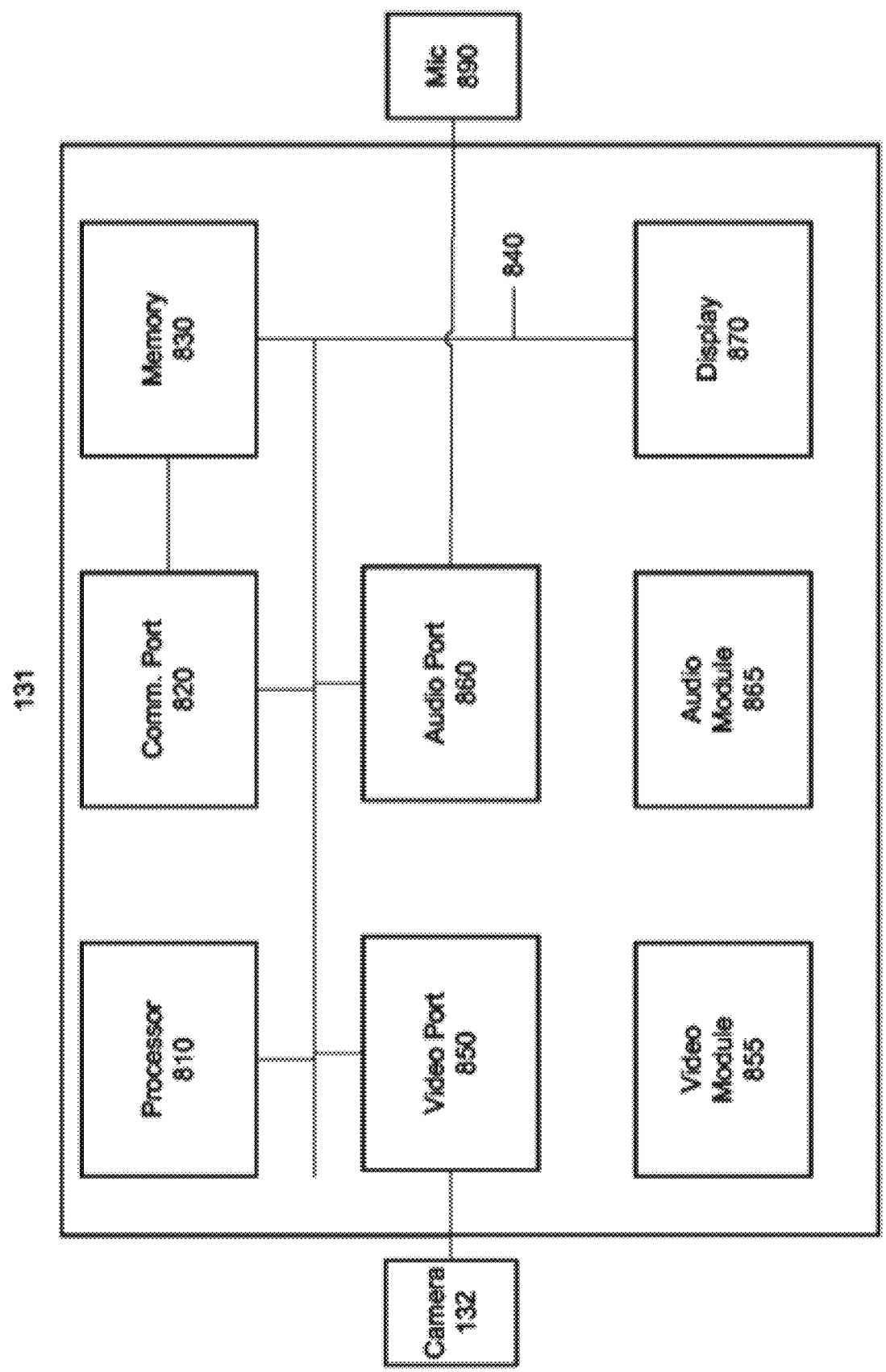
FIG. 8 is a schematic block diagram of a camera unit according to an embodiment of the invention.

FIG. 8 is a camera unit 131 according to an embodiment of the invention. The camera unit 131 may be housed in a portable device that may be brought around to various patients in the hospital 130. For example, the camera unit 131 may be housed in a wheeled cart or a self-propelled robotic unit. The camera unit 131 may include one or more computers. The one or more computers may include a processor 810, a communication port 820 which may be configured to connect to the network 100, a memory 830, a video port 850 to which a camera 132 may be connected, an audio port 860 to which a microphone 890 may be connected, a display 870, and/or other hardware, which may be interconnected by a bus 840. The ports may be any ports capable of exchanging data (e.g., Ethernet, USB, etc.). The one or more computers may include a video module 855, an audio module 865, a UI module 880, and/or other modules. Such modules may be software stored in memory 830 and executed on processor 810. Example functions of these modules are described in greater detail below.

Figure 2:
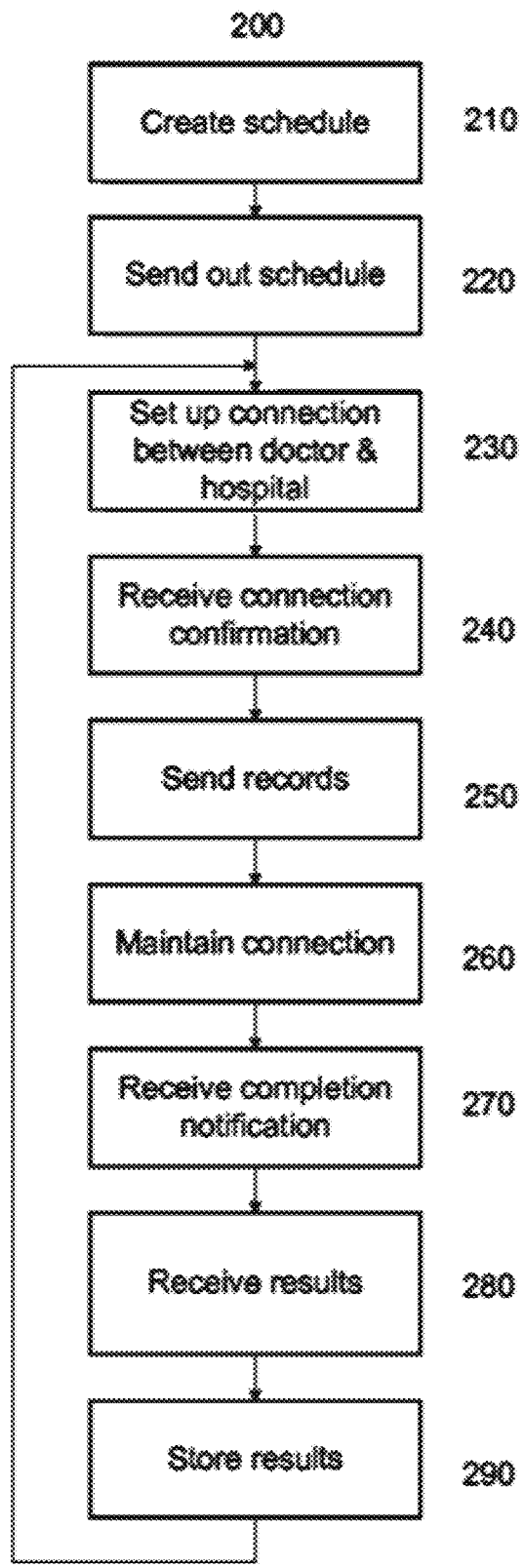
FIG. 2 is a flowchart of a session management process according to an embodiment of the invention.

FIG. 2 is a session management process 200 according to an embodiment of the invention. This process 200 may be performed by the CCC 110 to establish, maintain, and process remote evaluation sessions. Multiple hospitals 130 may request remote evaluation services from the CCC 110. These hospitals 130 may be geographically spread out (e.g., in different time zones) and may operate on different schedules. The CCC 110 scheduling module 650 may create a schedule 210 indicating when each hospital 130 is ready for remote evaluation. The schedule may include a start time for a particular remote evaluation in each hospital 130. The schedule may take into account a number of patients in an ICU and an estimated time for evaluation per patient to create an approximate duration for each hospital's 130 session. The CCC 110 may distribute this schedule 220 to doctor computers 120 connected to the CCC 110 via the network 100. The UI module 780 of a doctor computer 120 may cause the display 770 to show the schedule to the doctor, and the doctor may indicate that he or she is ready to perform a remote evaluation session via interaction with the UI module 780 using any input device. The doctor may be able to select a specific hospital 130 from among several hospitals 130 that are ready for remote evaluation. For example, if a doctor has previously performed remote evaluations at a specific hospital 130, he or she may wish to perform subsequent sessions. However, the same doctor need not necessarily perform sessions with the same hospital 130 every time. The CCC 110 may also automatically assign doctors to hospitals 130 based on the schedule (e.g., if hospital X is estimated to take 1 hour beginning at midnight, and doctor Y is not otherwise assigned in the midnight to 1 AM time slot, doctor Y may be assigned to hospital X by the CCC 110).

Figure 5:
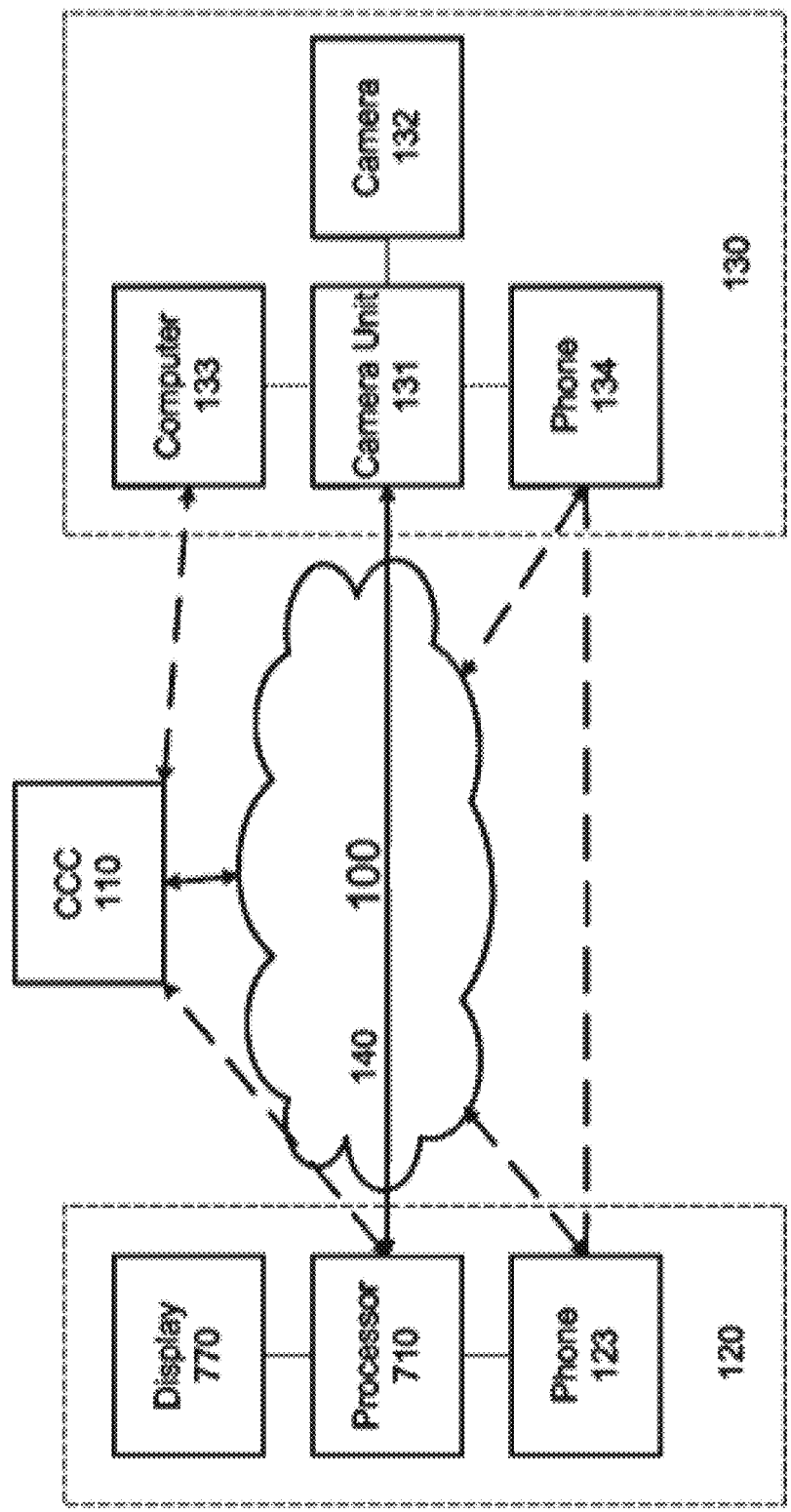
FIG. 5 is a schematic connection diagram according to an embodiment of the invention.

The doctor computer 120 may indicate the doctor's readiness at the start time for a hospital 130 and/or hospital 130 selection to the CCC 110, and the CCC 110 connection module 660 may set up a connection 230 between the doctor computer 120 and the hospital 130. FIG. 5 is a connection diagram 500 according to an embodiment of the invention. The hospital 130 may be equipped with a camera unit 131, as discussed above. The camera unit 131 may include a camera 132, and the camera unit 131 may capture video via the video port 850 and transmit the video to the doctor computer 120 via the communications port 820. Similarly, the camera unit 131 may capture audio via the audio port 860 and microphone 890 and transmit the audio to the doctor computer 120 via the communications port 820. The doctor computer 120 and camera unit 131 may be connected via the network 100 so that the doctor computer 120 may display images and/or video from the camera 132 on the display 770. Creating the connection may include establishing a connection with the connection module 660 of the CCC 110 and then handing off the connection so that the doctor computer 120 and camera unit 131 interact directly with one another via the network 100, without sending data through the CCC 110 after the handoff. The respective microphones 768, 890 and audio ports 760, 860 and/or the phone 123 may be used to establish an audio link between the doctor at the doctor computer 120 and individuals on site at the hospital 130, such as a nurse and/or patient, via the network 100. The connection between the doctor computer 120 and the camera unit 131 at the hospital 130 may be maintained through the CCC 110 (e.g., data may pass through the CCC 110) or through an independent network 100 connection (e.g., connection 140). The connection module 660 may monitor integrity of the connection during the session and may reestablish the connection if it breaks. The CCC 110 may facilitate additional communication, for example by providing a phone number for the hospital 130 to the doctor computer 120 and/or by providing a phone number for the doctor to the hospital 130. The hospital 130 may also include a phone 134 (e.g., an IP phone) which may be part of the camera unit 131 or separate from the camera unit 131. Thus, a doctor and a nurse could speak by phone in addition to interacting via the doctor computer 120 and camera unit 131, for example. The hospital 130 may also include additional computers 133, which may be used for interacting with the CCC 110, for example for data entry as described in greater detail below.

Returning to FIG. 2, once the connection is established, the connection module 660 of the CCC 110 may receive connection confirmation 240 from the doctor computer 120 and/or hospital 130. The data module 670 of the CCC 110 may send any medical records 250 that may be relevant to the remote evaluation session to the doctor computer 120. For example, records generated during prior remote evaluation sessions for the hospital 130 may be sent. If the remote evaluation session is for an ICU including multiple patients, the records may include information about each patient in the ICU gathered during the previous remote evaluation sessions. The CCC 110 may monitor and maintain the connection 260, for example by monitoring connection integrity and providing for reconnection if communication is broken. The doctor and hospital 130 personnel may perform the remote evaluation, and when the session is complete, the doctor computer 120 and/or hospital 130 may end the session. The CCC 110 may receive notification of session completion 270. The data module 670 of the CCC 110 may receive results of the remote evaluation session 280 from the doctor computer 120 and/or hospital 130 (e.g., via the hospital computer 133 or camera unit 131). For example, a doctor may proceed through a series of questions and perform a basic evaluation of patients in the ICU. The basic evaluation may include a visual evaluation of the patient facilitated by the video link between the camera 132 and doctor computer 120 display 770. Answers to the questions may be sent to the CCC 110. Example questions and specific evaluations are described in greater detail below. The results may also include an indication that a particular patient needs more specialized help. The CCC 110 may be able to refer the patient to more specialized help from a remote specialist, as discussed in greater detail below. The results may be entered into the doctor computer 120 via the UI and sent to the CCC 110, entered into a hospital 130 computer and sent to the CCC 110, and/or sent to the CCC 110 in some other way (e.g., faxed or phoned in) and entered into the CCC 110 on site. The CCC 110 may store the received results 290, and the results may be available for subsequent remote evaluation sessions at the hospital 130. After a remote evaluation session is completed, a doctor may move on to another hospital 130 for another session, and the process described above may be repeated. The CCC 110 may be able to perform session management 200 for multiple doctor computer 120 and hospital 130 connections at a time.

A remote evaluation session may include pointing a camera at a patient and making a brief general statement about the patient, identifying chief physiologic failure mode(s) for the patient, a doctor asking and hospital staff answering binary questions with respect to certain types of work that may be assessed on a daily basis (e.g., appropriate prophylaxis, nutrition, device management, etc.), and providing an opportunity for the hospital staff to solicit help and/or for the doctor to offer help.

Figure 3:
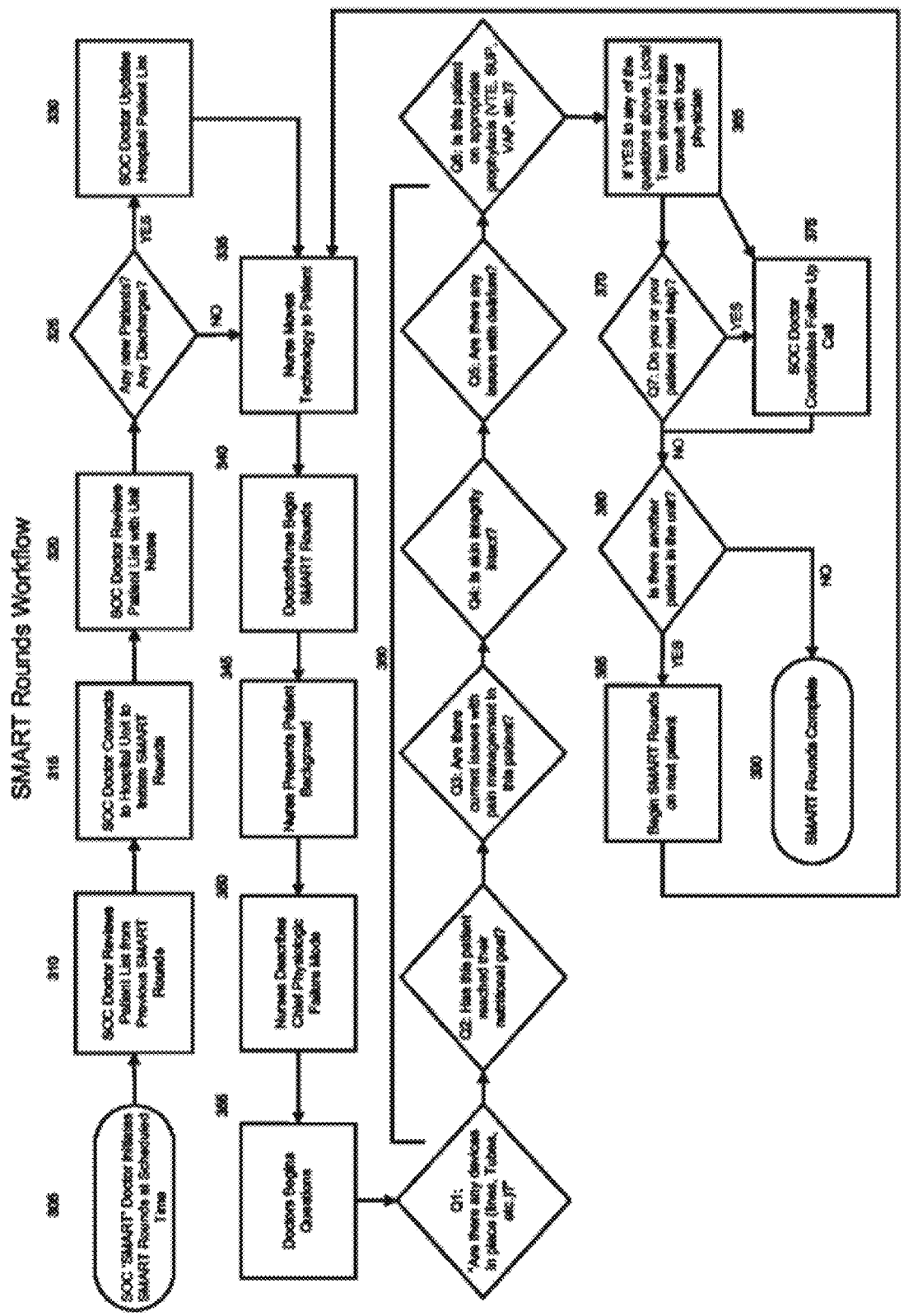
FIG. 3 is a flowchart of an evaluation workflow according to an embodiment of the invention.

FIG. 3 is a remote evaluation workflow 300 according to an embodiment of the invention. A doctor may log onto the remote evaluation system 305 via the doctor computer 120. The UI may present the doctor with a patient list and/or schedule for review 310, which may be provided by the CCC 110. The doctor and a specific care facility (e.g., a specific hospital's ICU) 315 may be connected, for example as described above with respect to FIG. 2. The doctor may review the patient list with a nurse at the facility 320. If there are new patients or discharges 325, the patient list may be updated 330. If there are no changes to the patient roster 325, the nurse may move the camera unit 131 to a first patient 335.

The remote evaluation session for the first patient may begin 340. As discussed above, the doctor may be provided with a video feed of the patient. Similarly, a camera 758 at the doctor computer 120 and a display 870 at the camera unit 131 may provide a video feed of the doctor to the patient and/or nurse in some embodiments. In the session, the nurse may present the patient's background 345 and chief physiologic failure mode 350 to the doctor, for example. The doctor may ask questions 355. For example, in an ICU setting, questions 360 may include whether there are any devices (e.g., lines, tubes, etc.) in place, whether the patient has met nutritional goals, whether there are any pain management issues, whether skin integrity is intact, whether there are issues with delirium, and/or whether the patient is on appropriate prophylaxis (e.g., venous thromboembolism, stress ulcer, ventilator-associated pneumonia, etc.). The doctor may ask questions of the nurse and may or may not interact with the patient. Of course, the system may be used in any setting for any clinical specialty.

Once the questions are asked and answered, immediate issues may be identified, and a consult with a local physician may be ordered 365. For example, in the ICU setting, if any urgent issues are identified through doctor questioning, the nurse may initiate a consult with a local physician and/or the doctor may coordinate a follow-up call, for example a remote consultation with a specialist 375. The doctor may also ask if the on-site personnel (e.g., the nurse) or the patient needs help 320. If so, the doctor may coordinate a follow-up call 375. The follow-up call may be coordinated through the doctor's computer 120 UI module 780. For example, the doctor may be able to indicate that follow-up is needed, and this information may be transmitted to the CCC 110 scheduling module 650. The CCC 110 scheduling module 650 may automatically search a listing of specialists in the memory 630 for available specialists to handle the follow-up and assign and notify one of the specialists, may automatically contact the hospital 130 to suggest the follow-up, and/or may direct call center personnel to coordinate the follow-up manually. Through this process, the doctor may provide care management by exception (e.g., the doctor may identify problems that need additional attention, and may not necessarily perform a thorough rounding examination on each patient). Management by exception may allow the remote evaluation sessions to be relatively brief, but may allow patient care to be escalated by remote and/or local follow-up if necessary. Thus, significantly fewer doctor computers 120 than hospitals 130 may be able to interact with the CCC 110 at any given time while still providing coverage of all hospitals 130.

If there are more patients to visit 380, a remote evaluation session for the next patient may begin 385. This session may proceed as described above. If there are no more patients, remote evaluation may be completed for this location. As described above, the CCC 110 may receive indication of completion and/or session results. The doctor may log off or remotely visit a different location for another remote evaluation session.

The background information and answers to questions may be used to generate a data sheet for each patient.

FIGS. 4A and 4B are opposite sides of a data sheet 400 ("intensive care smart sheet" in this example) according to an embodiment of the invention. Although FIGS. 4A and 4B are directed to intensive care, this system may be employed for any clinical specialty by changing to an appropriate SMARTsheet. As shown in FIG. 4A, the data sheet 400 may enable the doctor and/or nurse to enter information generated by the remote evaluation session. The data sheet 400 may be placed in the patient's chart for use by local medical personnel and/or for comparison with past and/or future remote evaluation sessions for the patient. The data sheet 400 may be used as a template for gathering information for storage by the data module 670 into the memory 630 of the CCC 110. For example, the doctor may fill in data sheet 400 fields in the doctor computer 120 UI, and the doctor computer 120 may send the data to the CCC 110. The nurse or another individual at the hospital 130 may fill in data sheet 400 fields in a hospital 130 computer, and the hospital 130 computer may send the data to the CCC 110 data module 670. The nurse or another individual at the hospital 130 may fill in a physical data sheet and fax it to the CCC 110. The CCC 110 data module 670 may gather the information from the faxed data sheet automatically (e.g., by optical character recognition or some other method) or via manual entry into a CCC 110 computer via an input device interaction with the UI module 680.

FIG. 9 shows a SMART sign out sheet that may be used at the end of a shift of a health care professional (e.g., physicians, nurses, assistants, etc.) local to the patient. This allows the health care professional to document the patients that they are responsible for and transmit this data to the CCC 110 for the next shift.

The data sent back to the CCC 110 (including data from the SMARTsheet (FIGS. 4A and 4B) and SMART sign out sheet (FIG. 9) may be used to help identify meta-trends. For example, the data may be used to identify common physiologic failure modes (see FIG. 4B), common failure points in process, common breakdowns in process metrics, which patients or situations require the most help, etc. In performing remote evaluations, data collected as described above may reveal trends applicable to individual hospitals. If a hospital has consistent issues (e.g., devices inappropriately left in place, prophylaxis problems, etc.), these may be identified if they are frequently reported by remote doctors. In another example, the data may reveal that a hospital's staff consistently does not ask for help, but remote doctors frequently identify a need for further help. As a result, hospital troubleshooting may be performed, and hospital efficiency/effectiveness may be improved. This ongoing documentation may also be used in facilities/programs with metrics for quality/safety/Joint Commission standards. In an individual patient example, a patient's records accrued over multiple remote evaluation sessions may be compiled in the CCC 110 database and may be viewed, for example via the UI of the doctor computer 120. When a doctor is performing a remote evaluation session involving the patient, the doctor may be able to use trends found in the patient's past data to evaluate whether an observation of the patient represents a problem that should be flagged for follow-up or is merely indicative of the patient's base condition. Such data may be employed as a research tool to assess various metric and to suggest new ways to potentially affect the treatment of patients and quality of patient care.

To effectuate this trend analysis over multiple remote evaluation sessions involving multiple patients, the patient's past data is collected, consolidated, evaluated and presented via a TeleICU dashboard that allows tele-intensivists using the remote medical evaluation platform described above to collaborate with the onsite clinical team to develop care plans, provide daily assessments with proactive, structured interactions. More specifically, multiple patient records are accrued over a rolling period of remote evaluation sessions, are compiled in the CCC 110 database, analyzed on an institutional level, then made available in at the hospital 130 or doctor computer 120 on a dynamic TeleICU dashboard.

The present system employs a consult documentation module such as Microsoft Dynamics® CRM, which may be used as a means to collect data, which are scrubbed and staged into "cumulated data" in CCC 110 data warehouse.

The institutional analysis comprises a two-stage heuristic analysis herein referred to as a Care Analysis, that uses a specific array of quantitative measures derived from medical encounters including labs, vitals, and most importantly follow-up information derived from remote medical assessments shown in FIG. 4. At a first stage five specific quantitative measures are derived from post-encounter medical assessments are scored and compiled into a qualitative care score, such as the "Patient Care Score" shown in FIGS. 10A and 10B. At a second stage four specific quantitative measures are derived from post-encounter medical assessments, scored and combined with the care score into an overall facility score, such as the "Charlotte Score" shown in FIGS. 11A and 11B. This Charlotte Score represents actionable data precisely because it can be used to assess different processes and outcomes as well as can be linked to a variety of different processes and outcomes such as patient outcomes, patient-related care processes, institutional goals for care, future patient outcomes, etc. It is predictive in the sense that it allows prediction of current patient outcomes as well as future patient outcomes. The Charlotte Score is prescriptive in the sense that it indicates what needs to change to improve those outcomes. Both the Patient Care Score and Charlotte Score are compiled in real time over a rolling time period, preferably six months and displayed on a novel dashboard that provides user-defined filters to filter both the Patient Care Score, Charlotte Score and individual metrics. Moreover, the institutional analysis and two-stage "Charlotte Score" heuristic is multi-dimensional inasmuch as it can be selectively applied across corporate entity, division within that entity, and/or by individual facility.

The result is a continuous measure of Patient Care and overall. Charlotte Score on an institutional level computed on a real-time basis across all conditions, diseases, and care settings. The care assessment may be used to help identify trends, for example, common physiologic failure modes, common failure points in process, common breakdowns in process metrics, which patients or situations require the most help, etc. If a hospital has consistent issues (e.g., devices inappropriately left in place, prophylaxis problems, etc.), these may be identified if they are frequently reported by remote doctors. In another example, the data may reveal that a hospital's clinical staff consistently do not seek help despite a remote doctor's frequent indication of need for help. As a result, hospital troubleshooting may be performed, and hospital efficiency and effectiveness improved. This ongoing application of rolling real time analytics yields valuable metrics for quality/safety/integrity of care.

The CCC 110 data module 670 is programmed to mine patient electronic health information (EHI) from multiple remote electronic health record (EHR) sources and cumulate that data. In addition, assessment data is entered via the CCC 110 data module 670, and is accrued over multiple remote evaluation sessions, and compiled in the CCC 110 database. The CCC 110 data module 670 extracts common data elements and performs a scrubbing operation to ensure integrity (dupes are eliminated, and data elements are screened against pre-defined "filters" to ensure completeness).

As indicated above the data sent back to the CCC 110 includes data from the SMARTsheet (FIGS. 4A and 4B) and SMART sign out sheet (FIG. 9) and/or data sheet 400. In addition to each patient's medical records, the foregoing telemedicine data may be used to collect information generated by the remote evaluation sessions post-encounter. The CCC 110 data module 670 may gather the information from the faxed data sheet automatically (e.g., by optical character recognition or some other method) or via manual entry into a CCC 110 computer via an input device interaction with the UI module 680.

Preferably the SMARTsheet (FIGS. 4A and 4B) includes at least the following data:
1. General orienting sentence on the patient (e.g. 62 year old man admitted for pneumonia):
2. Physiologic Deterioration
3. Process Metrics:
   Any devices in place (lines, tubes, etc.)?
   Are any or all of them still necessary?
   Has this patient reached their nutritional goal? If NO—has this been addressed?
   Are there current issues with pain management in this patient? If YES—have these been addressed?
   Is skin integrity intact? If NO—is this being addressed?
   Are there issues with delirium? If YES are these being addressed?
   Is this patient on appropriate prophylaxis (VTE, SUP, VAP, etc.)? If NO—are these being addressed?
   Has the patient been mobilized?
   Are there ethical or care philosophy or family issues?
4. Does patient need help? If YES—then coordinate a consult for the patient.

From the foregoing four specific quantitative measures are scored and combined into a Patient Care Score. The four quantitative measures include:
Total number of assessments (Antot)
Total number of skin integrity issues (Sntot) and number being addressed (Snadd);
Total number of delirium issues (Dntot) and number being addressed (Dnadd);
Number of patients mobilized (Mn);
Number of patients on appropriate prophylaxis (Pn).

This, for example, yields the following quantitative measures compiled over a six month period:
Antot=1500
Mn=390
Pn=1200
Out of 50 issues related to skin integrity, 38 were being addressed: Sntot=50 and
Snadd=38;
Out of 100 issues related to delirium, 26 were being addressed: Dntot=100 and
Dnadd=26.

Figure 10A:
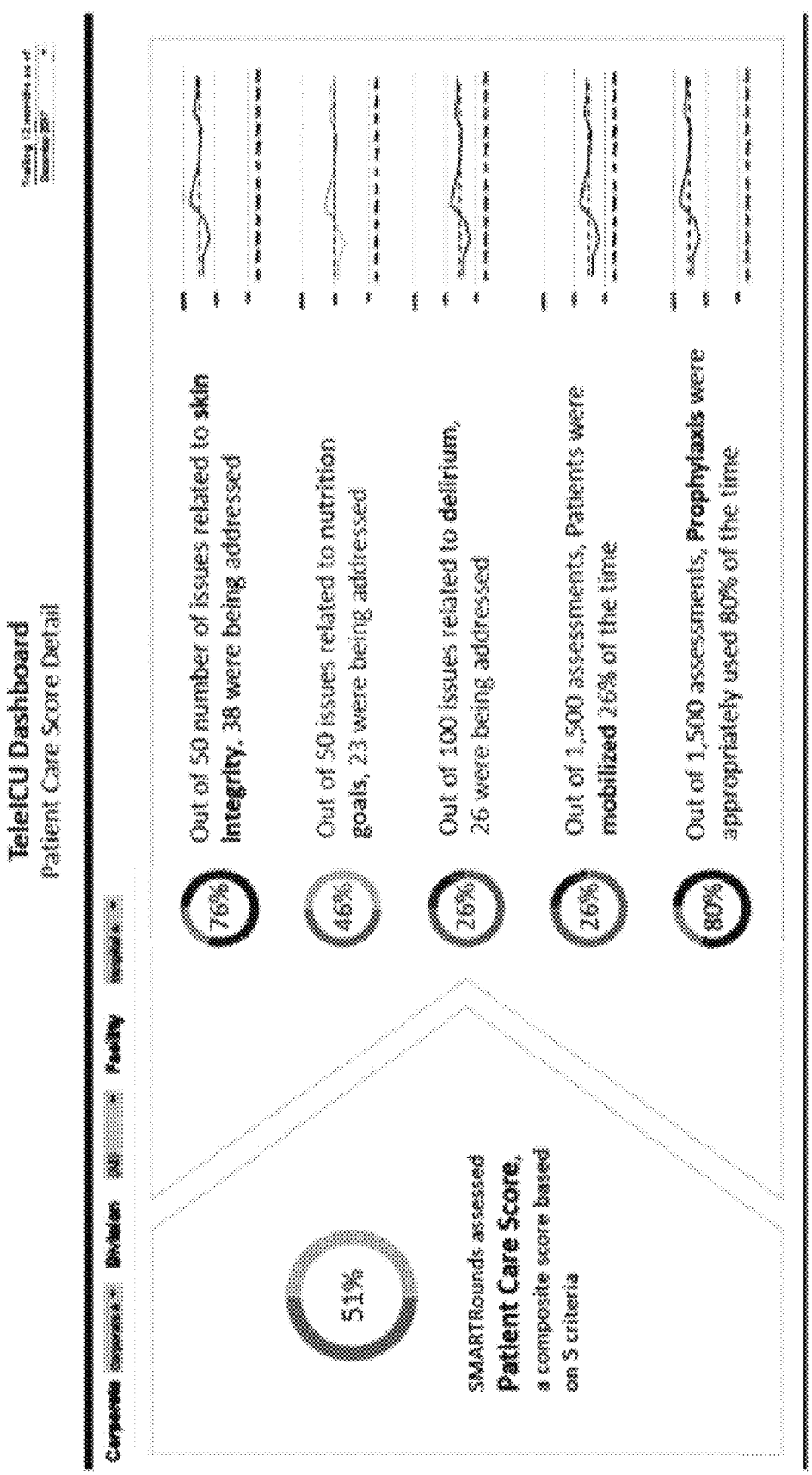
FIGS. 10A and 10B are screens of an example dashboard for a patient care score user-interface illustrating how a consult coordination center can assesses various treatment status indicators and calculate the composite care score based on the treatment status indicators, according to an embodiment of the invention.
Figure 10B:
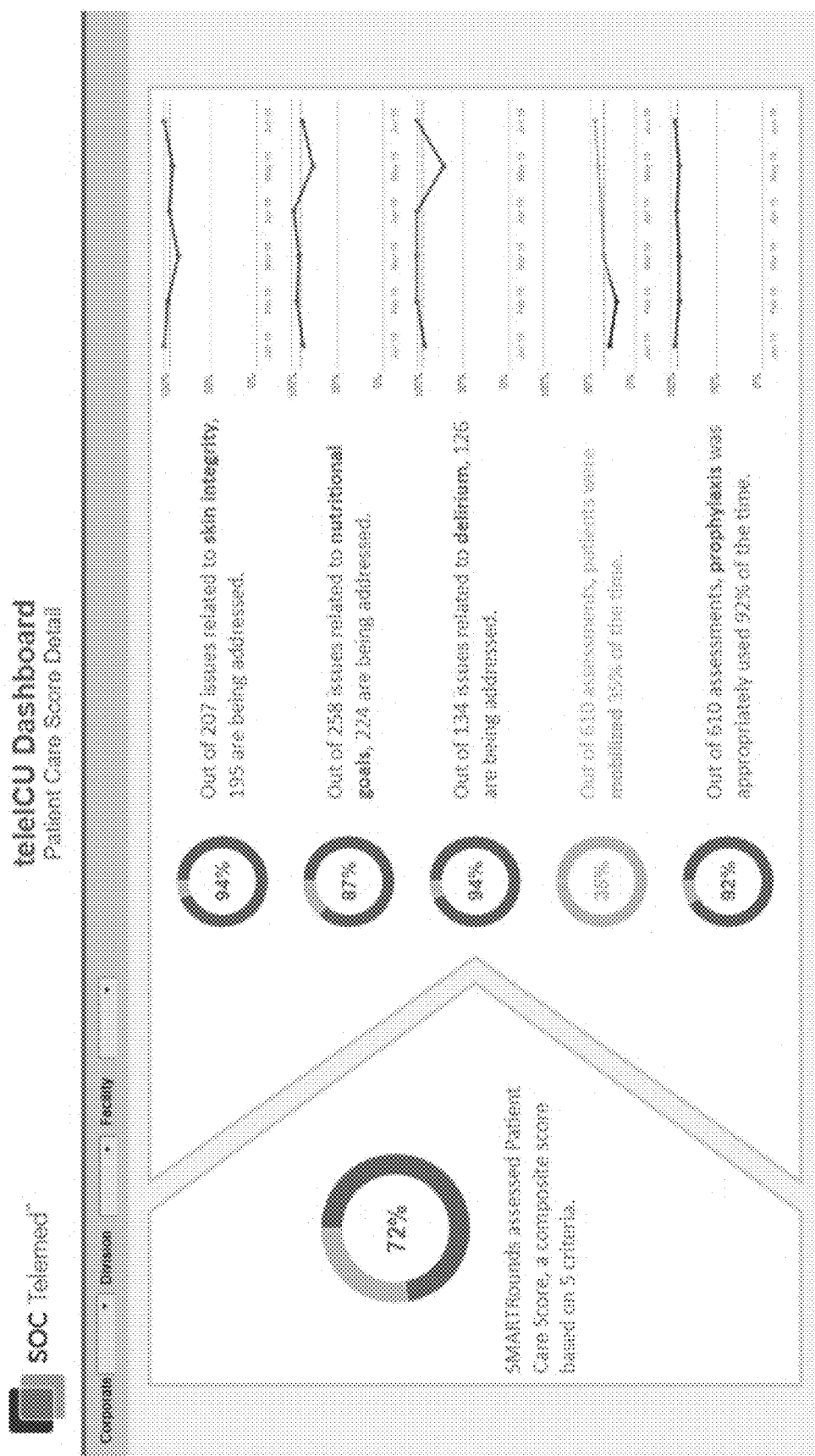

FIGS. 10A and 10B are screens of an example dashboard for a patient care score user-interface illustrating how a consult coordination center can assesses various treatment status indicators and calculate the composite care score based on the treatment status indicators, according to an embodiment of the invention. Importantly, each parameter may be displayed textually, e.g. "Out of 50 number of issues related to skin integrity, 38 were being addressed", plus graphically (at right) over time, and as a numerical percentage displayed inside a circular percentage indicator. The CCC 110 may then apply intelligent weighting to the treatment status indicators and present a composite care score (at left) as a numerical percentage displayed inside a circular percentage indicator. Treatment status indicators may include, for example, an indicator of how the first facility is addressing skin integrity issues, an indicator of how the first facility is addressing nutritional goals, an indicator of how the first facility is addressing delirium-related issues, an indicator of how the first facility is addressing patient mobilization, and an indicator of how the first facility is addressing prophylaxis issues.

The second stage of the heuristic analysis may include computing quantitative treatment compliance indicators derived from post-encounter medical assessments and combining them with the care score into an overall facility score, such as the Charlotte Score. The treatment compliance indicators can be based quantitative measures including:
Total number of evaluation recommendations followed (Rtot)
Total number of recommended evaluations completed (Etot)
Total number of recommended downgrades completed (DGtot)

Total number of recommended device removals completed (REMtot)

This, for example, may yield the following quantitative measures compiled over a six month period:

Rtot=40
Etot=25
DGtot=10
REMtot=32

Figure 11A:
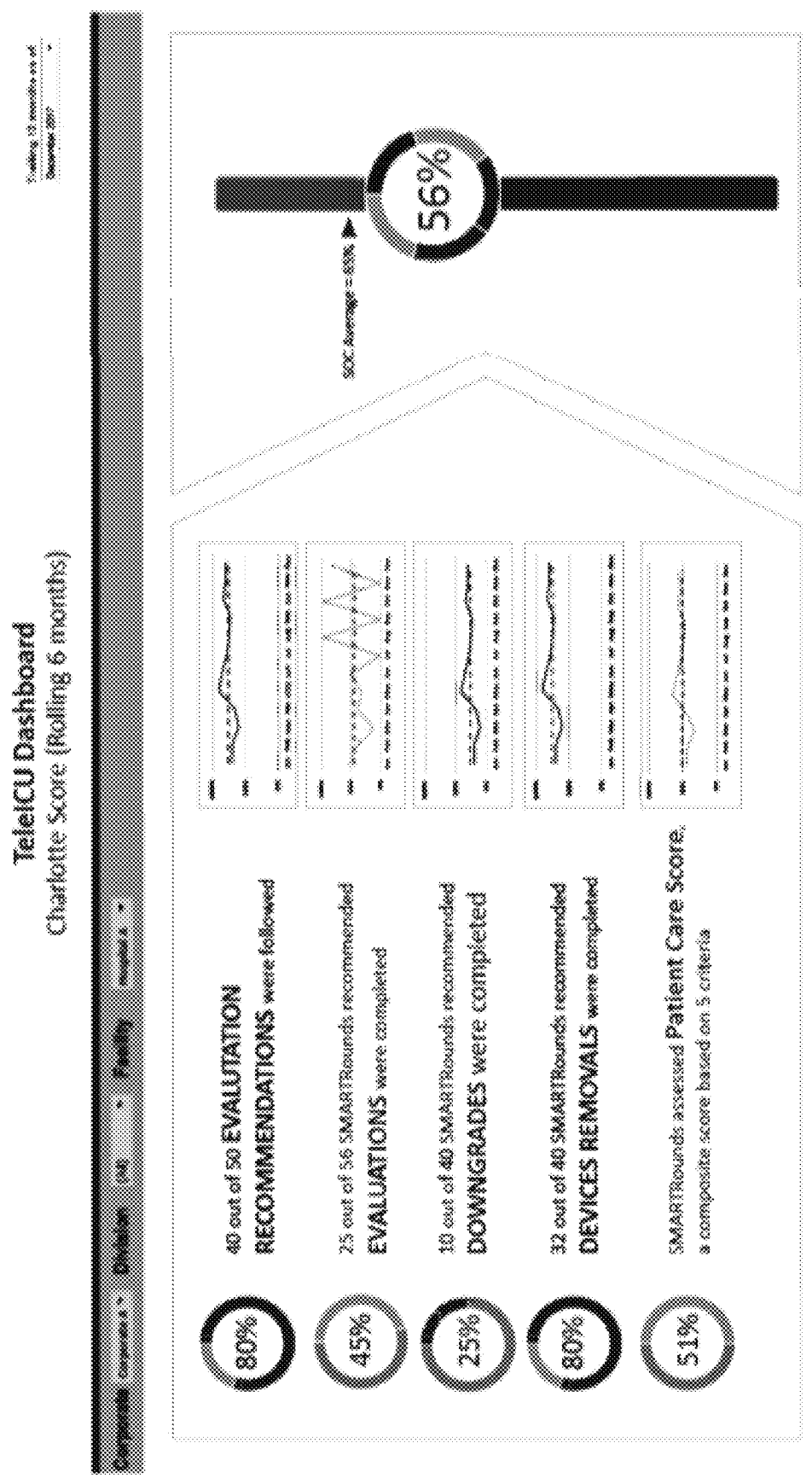
FIGS. 11A and 11B are a screens of an example dashboard for a care assessment user-interface illustrating how a consultant coordination center can assess various treatment compliance indicators and calculate the composite facility score based on the treatment compliance indicators and the care score, according to an embodiment of the invention.
Figure 11B:
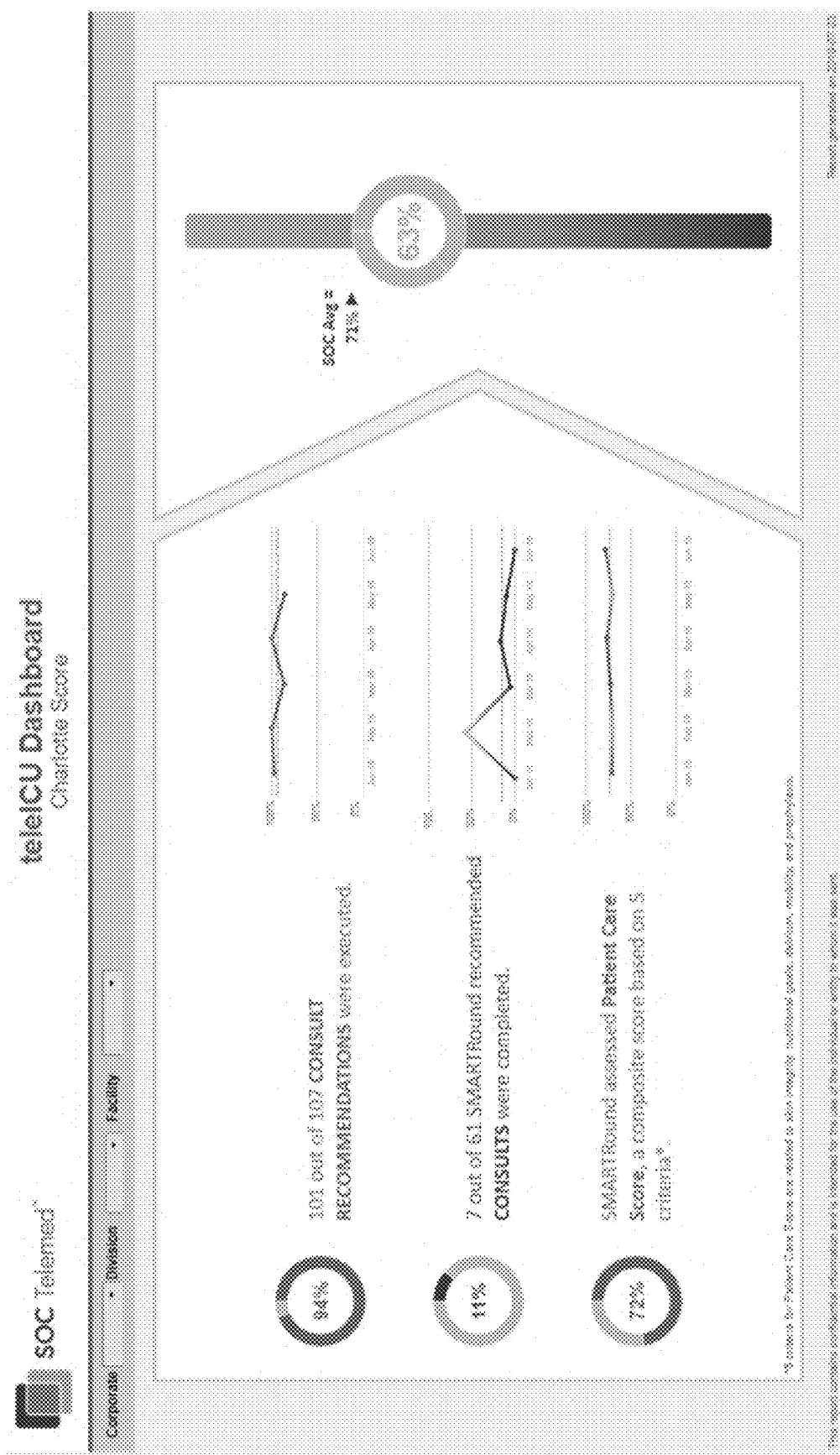

FIGS. 11A and 11B are a screens of an example dashboard for a facility score user-interface illustrating how a consultant coordination center can assess various treatment compliance indicators and calculate the composite facility score based on the treatment compliance indicators and the care score, according to an embodiment of the invention. Again, each parameter may be displayed textually, e.g. "40 out of 50 EVALUATION RECOMMENDATIONS were followed", graphically (at right) over time, and as a numerical percentage displayed inside a circular percentage indicator. The CCC 110 then can then compute an average of the treatment compliance indicators along with the care score, and present a composite score facility score (at right) as a numerical percentage displayed inside a circular percentage indicator. Treatment compliance indicators may include, for example, an indicator of whether a consult recommendation for the first patient was executed, an indicator of whether a recommended consult for the first patient was completed, an indicator of whether a recommended treatment downgrade for the first patient was completed, and an indicator of whether a recommended medical device removal for the first patient was completed.

Both the care score and facility score can be compiled in real time over a rolling time period, preferably six months. As seen at the top of FIGS. 10A, 10B, 11A, and 11B dashboard provides drop-down user selection filters to filter both the care score, facility score, treatment status indicators, and treatment compliance indicators by various comparison criteria, such as corporate entity, division within that entity, and/or by individual facility.

Figure 12A:
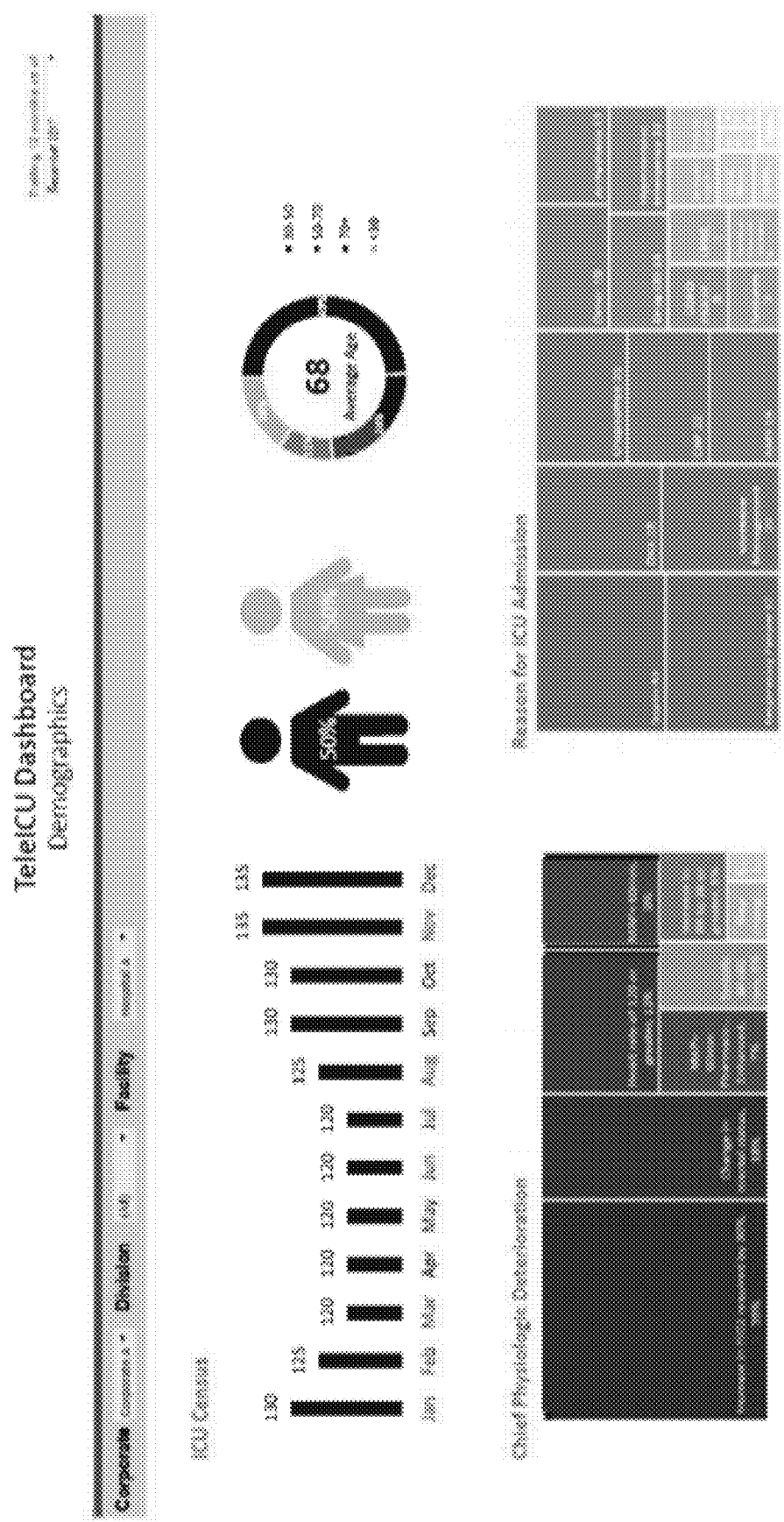
FIGS. 12A and 12B are screens of an example dashboard for a demographics user-interface according to an embodiment of the invention.
Figure 12B:
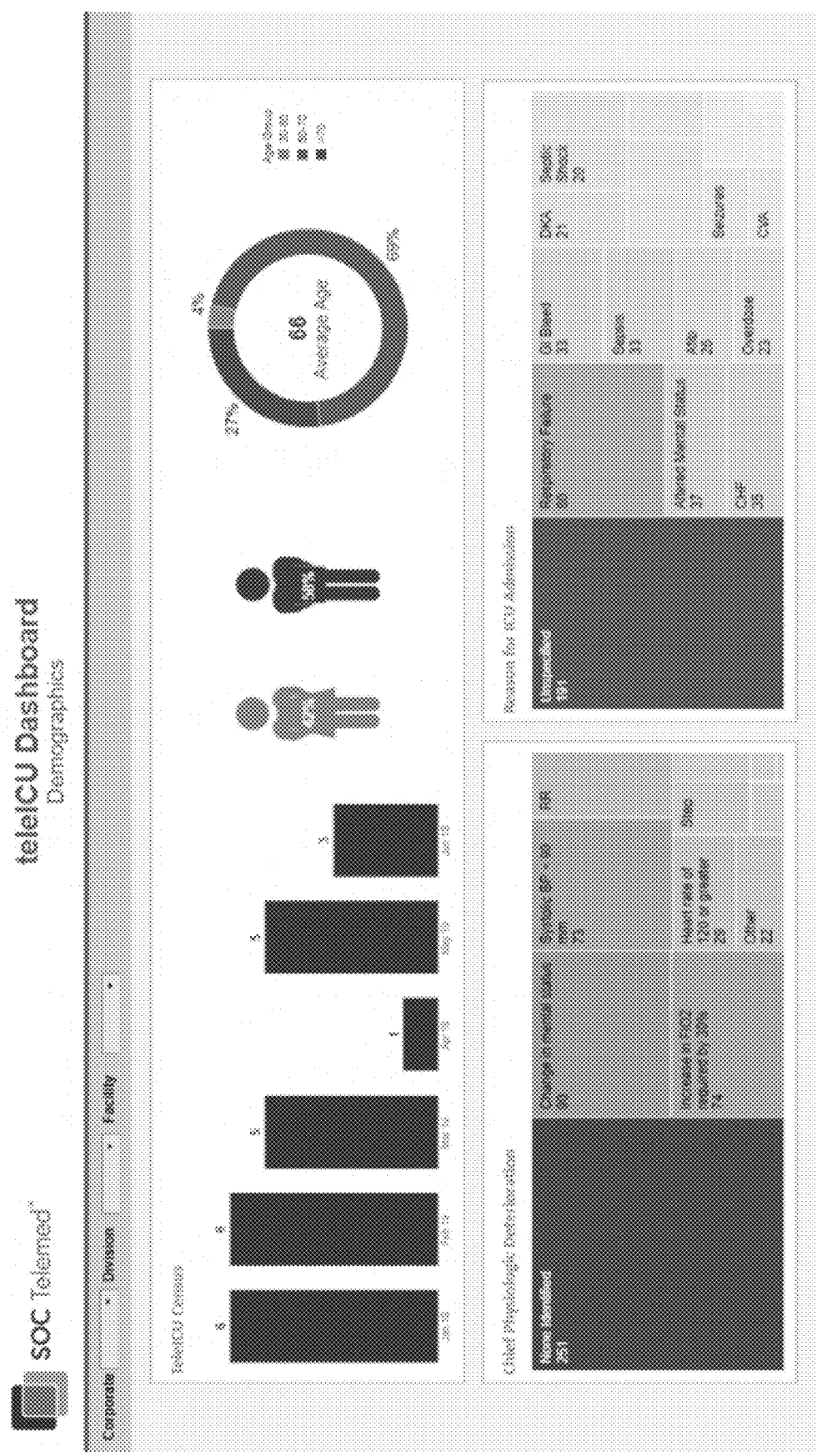

The system user-interface may also provide several additional metrics for the selected corporate entity. For example, FIGS. 12A and 12B are screens of an example dashboard for a demographics user-interface according to an embodiment of the invention. As shown, the demographics page may present an ICU Census (top left), Male/Female ratio and age averages (top right), Chief Physiologic Deterioration (lower left), and Reason for ICU Admission (lower right).

Figure 13A:
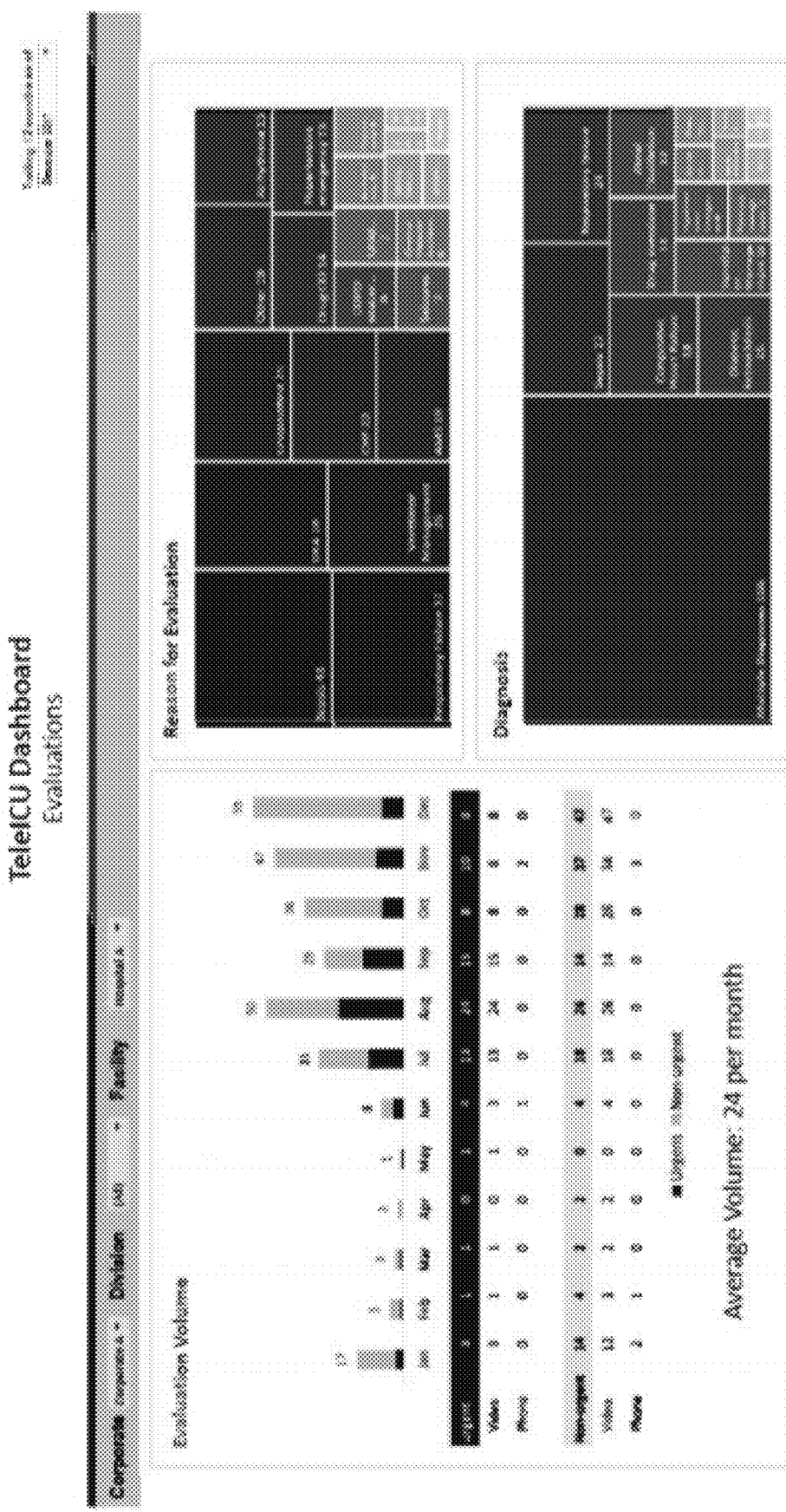
FIGS. 13A and 13B are screens of an example dashboard for an evaluation and consult user-interface according to an embodiment of the invention.
Figure 13B:
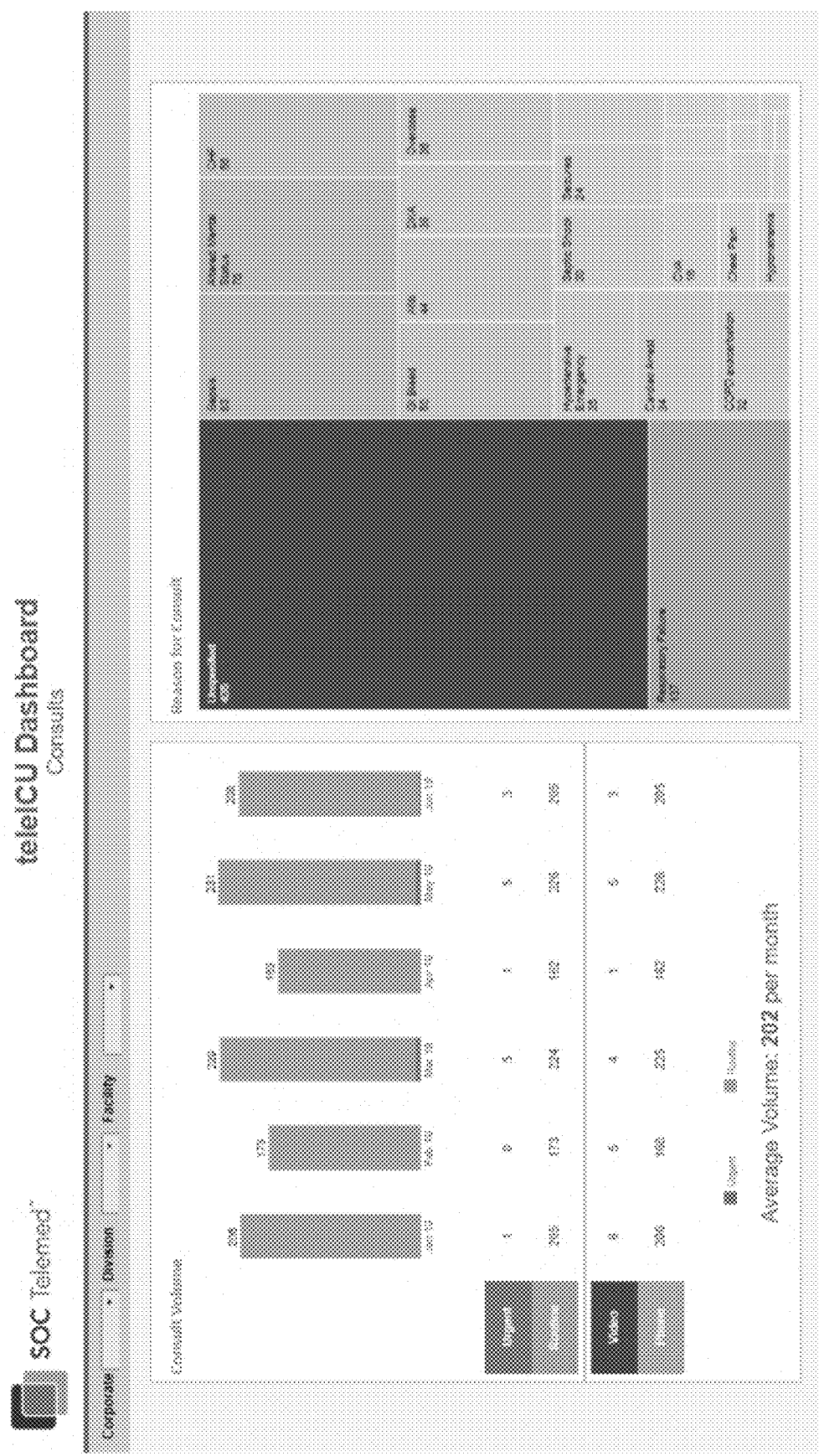

FIGS. 13A and 13B are screens of an example dashboard for an evaluation and consult user-interface according to an embodiment of the invention. As shown the evaluation and consult pages may present Evaluation volume (top left) as a monthly bar chart broken down by urgent versus non-urgent and video versus phone. In addition, the reasons for each evaluation may be presented as a % Statistical Visualization (top right). As indicated above the present system may also employ a consult documentation module 670 in a third party software such as Microsoft Dynamics to collect data, which can be scrubbed and staged into "cumulated data" in CCC 110 database, such as a data warehouse. Care assessment data can be entered via the CCC 110 data module 670 which may extract common data elements and perform a scrubbing operation to ensure integrity (dupes are eliminated, and data elements are screened against pre-defined "filters" to ensure completeness). In some embodiments, only after this scrubbing operation is the data accrued and compiled in the CCC 110 database, accruing over multiple remote evaluation sessions. The corresponding diagnoses may also presented as a % Statistical Visualization (bottom right).

Figure 14A:
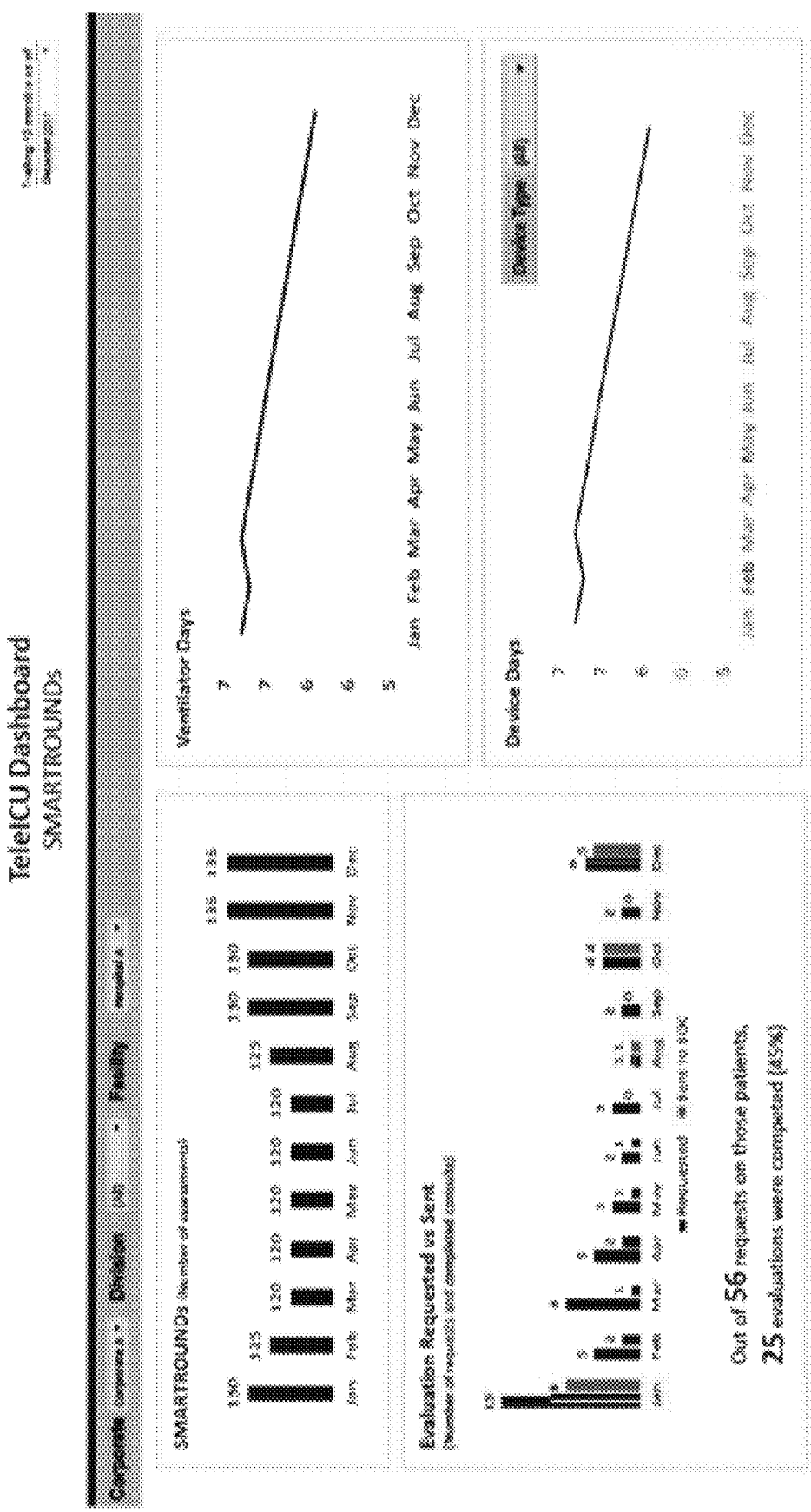
FIGS. 14A and 14B are screens of an example dashboard for a SmartRounds user-interface according to an embodiment of the invention.
Figure 14B:
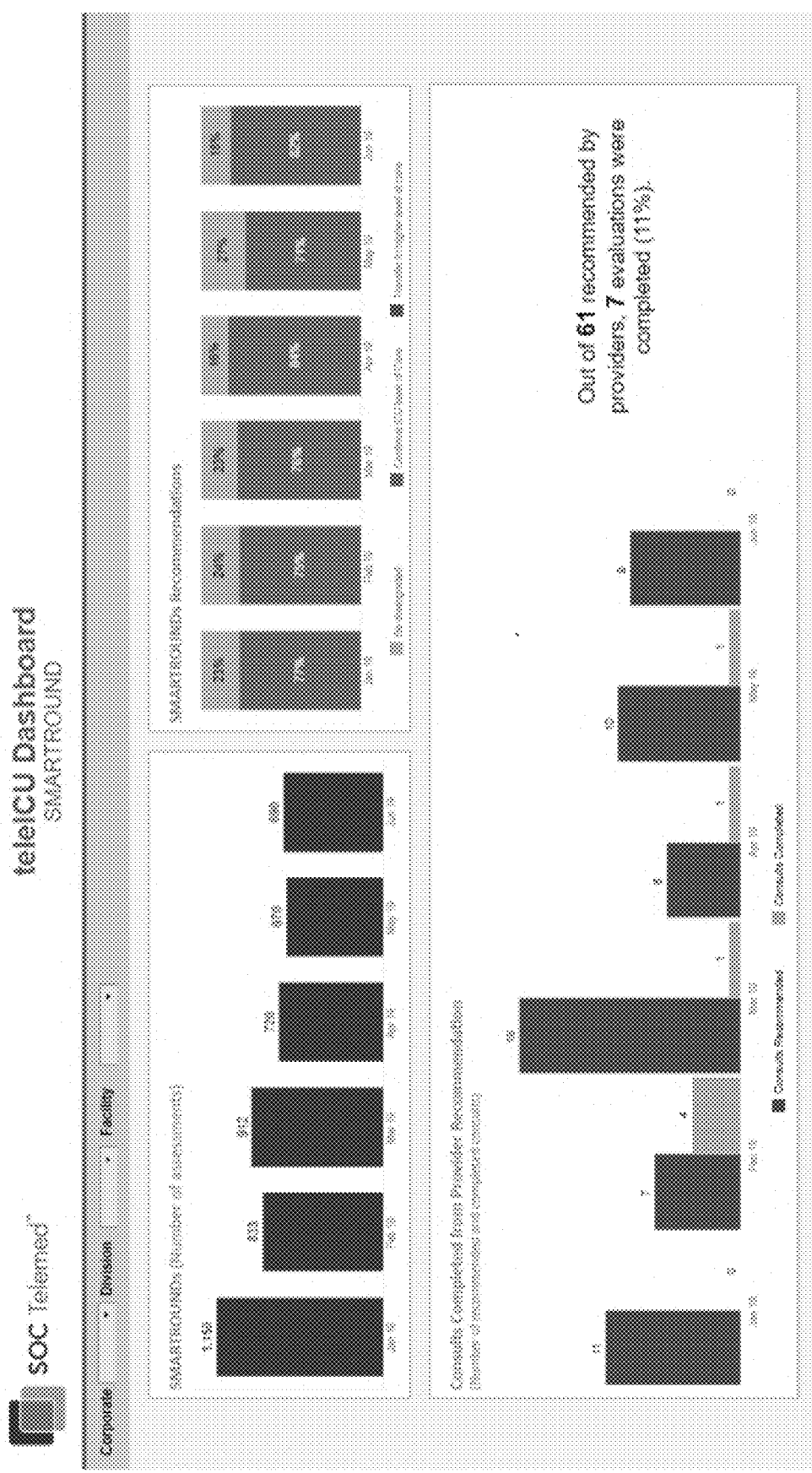

FIGS. 14A and 14B are screens of an example dashboard for a SmartRounds user-interface according to an embodiment of the invention. As shown the SmartRounds page may present the Assessment volume (top left) as a monthly bar chart with evaluations requested versus completed (bottom left). In addition, average per-patient days on a ventilator can be presented as a graph (top right) and average per-patient device days is presented as a graph (bottom right). In the latter, the graph may include a "device type filter" which allows selective display of average per-patient specific device days.

The present system may refine the facility score over time to correlate with patient outcomes such as mortality, length of stay, number of transfers etc. The facility score can be correlated for a hospital ICU with patient outcomes, such that the score is a good proxy to predict that hospital's patient outcomes (e.g., when a hospital's Charlotte Score is X %, the mortality will likely be Y %). This makes the facility score both predictive (allowing prediction of current patient outcomes as well as future patient outcomes) and prescriptive (indicating what needs to be changed to improve outcomes). Moreover, the institutional analysis and two-stage facility score heuristic is multi-dimensional inasmuch as it can be selectively applied across any institutional unit. This way the score can be provided to hospital as a prescriptive measure so that hospital can focus on certain areas of care to make a quicker gain in patient outcomes in the face of limited resources.

As indicated above, the CCC 110 data module 670 may be programmed to mine patient EHI from multiple remote EHR sources, cumulate that data, and make the data usable for heuristic analysis. This may entail entails gathering data from multiple sources at a different point of time, and aggregating, consolidating, cleansing, and removing obvious errors to standardize the data. The foregoing data cumulation can require filtering through predefined data filters in order to make the cumulated data accessible/digestible. As a result, embodiments of this invention may provide a prescriptive recommendation that a hospital can easily implement in their everyday patient care to make a high/quick/positive impact to patient outcomes.

Figure 15:
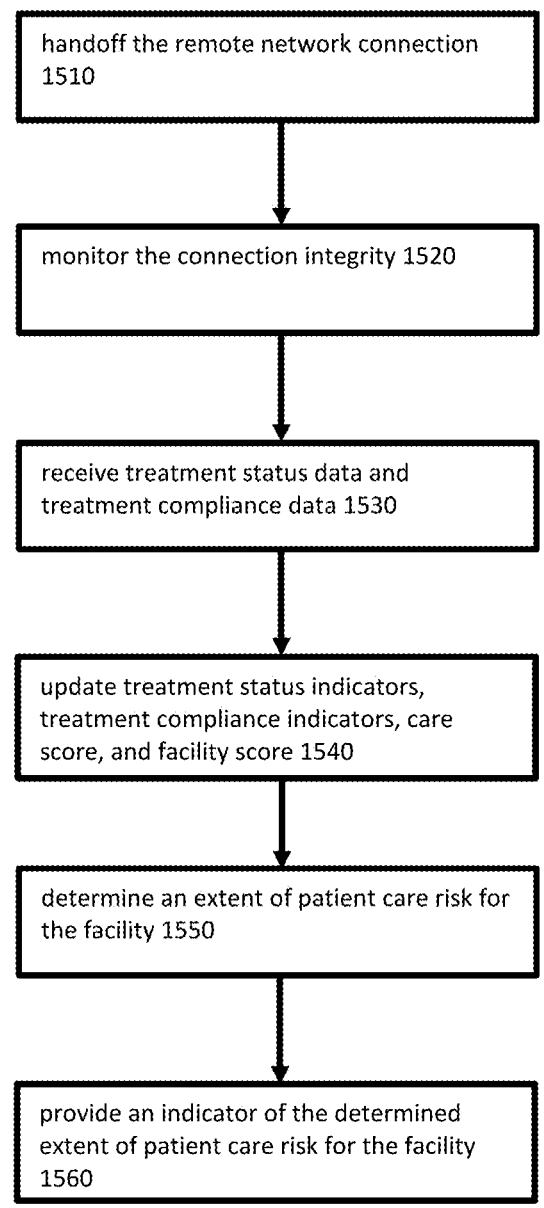
FIG. 15 is a flowchart showing an example procedure for providing a health care facility an indicator of a determined extent of patient care risk, according to an embodiment of the invention.

Systems according to embodiments of the invention can use treatment status indicators, treatment compliance indicators, care scores, and facility scores from the set of facilities connected to the system to determine an extent of patient care risk for a particular facility. For example, FIG. 15 is a flowchart showing an example procedure for providing a health care facility an indicator of a determined extent of risk, according to an embodiment of the invention. The system can determine an extent of patient care risk for a particular facility and notify the facility, such as by providing in indicator on the system's dashboard interface for the facility.

As shown in FIG. 15, CCC 110 computer can establish a remote network connection between a health care professional computer 120 and a health care facility computer 130. The remote network connection may be, for example, any one or more of an audio/video connection, a video connection, an audio connection, a health level 7 connection, an electronic medical record connection, or any other network connection suitable for the purposes of this invention. The CCC 110 computer can handoff the remote network connection to the remote health care professional computer 120 and facility computer 130 at 1510 and continue to monitor the integrity of the network connection at 1520. The remote health care professional can assess the patient over the connection, and at 1530 the CCC 110 computer can receive treatment status data and treatment compliance data for the facility that has been collected from the assessment of the patient.

According to embodiments of this invention, treatment status data can include an indicator of whether the patient's skin integrity is being addressed, an indicator of whether nutritional goals for the patient are being addressed, an indicator of whether the patient's delirium-related issues are being addressed, an indicator of whether the patient's mobilization is being addressed, and an indicator of whether prophylaxis for the patient is being addressed.

According to embodiments of this invention, treatment compliance data can include an indicator of whether a consult recommendation for the patient was executed, an indicator of whether a recommended consult for the patient was completed, an indicator of whether a recommended treatment downgrade for the patient was completed, and an indicator of whether a recommended medical device removal for the patient was completed.

The CCC 110 computer can update various metrics based on the received treatment status data and treatment compliance data at 1540. For example, the CCC 110 computer can access a record for the facility storing treatment status indicators, such as how many skin integrity issues had been identified and how many of such issues were being addressed. The CCC 110 computer may receive treatment compliance data from the assessment of the patient over the remote connection that indicates the patient has a had an identified skin integrity issue but that the issue had not been addressed by the facility. The CCC 110 computer can update the treatment status indicator based on the treatment status data by increasing the number of total identified skin integrity issues by one and keeping constant the total number of skin care integrity issues being addressed by the facility. As a result, the treatment status indicator may also indicate a lower overall percentage of identified skin integrity issues being addressed.

The CCC 110 computer can also update treatment compliance indicators for the facility at 1540 based on received treatment compliance data. For example, the CCC 110 computer can access a record for the facility storing treatment compliance indicators, such as how many treatment recommendations had been identified and how many of such recommendations were being addressed. The patient may have previously been recommended to have an evaluation for a particular condition, such as sepsis. The CCC 110 computer may receive treatment compliance data from the assessment of the patient over the remote connection that indicates the recommended evaluation had not been completed. The CCC 110 computer can update the treatment status indicator based on the treatment compliance data by increasing the number of total evaluation recommendations and keeping constant the number of total evaluation recommendations followed by the facility. As a result, the treatment compliance indicator may also indicate a lower overall percentage of evaluation recommendations being followed.

The CCC 110 computer can also update a care score for the facility at 1540, such as a Patient Care Score. For example, treatment status indicators for the facility can be updated based on received treatment status data in accordance with any of the techniques described herein. The updated treatment status indicators can serve as the basis for updating the care score. For example, computing device 110 can calculate a mean or weighted average of the treatment status indicators to determine the care score. The CCC 110 computer can then update the care score by changing an indicator of the care score to reflect the newly calculated care score.

The CCC 110 computer can also update a facility score for the facility at 1540, such as a Charlotte Score. For example, treatment compliance indicators for the facility can be updated based on received treatment compliance data in accordance with any of the techniques described herein. The updated treatment compliance indicators can serve as the basis for updating the facility score. For example, computing device 110 can calculate a mean or weighted average of the treatment compliance indicators along with the updated care score to determine the facility score. The CCC 110 computer can then update the facility score by changing an indicator of the facility score to reflect the newly calculated facility score.

CCC 110 computer may calculate care scores based on treatment status indicators and facility scores based on treatment compliance indicators in accordance with any procedure suitable for the purposes of this invention. Also, facilities may configure customized procedures or formulae for calculating care scores and facility scores, according to embodiments of this invention. For example, a facility may assign weightings to certain treatment status indicators or treatment compliance indicators, which have greater importance in the context of the facility. As another example, CCC 110 computer may perform various data analysis processes and statistical techniques to determine weightings for certain treatment status indicators or treatment compliance indicators. Such processes and techniques may result in score calculations or facility score calculations that accurately reflect treatment outcome frequencies and the overall state of care of a facility.

In one example, a facility may realize significant negative treatment outcomes caused by the occurrence of sepsis in patients. For example, the facility's incidence rate of sepsis may be significantly higher than other comparable facilities due to serving a patient population that is more susceptible to sepsis. Thus, preventing the incidence of sepsis may be especially important to the facility. The a facility computer 130 may be presented with a user-interface by CCC 110 computer that provides options for weighting the contribution of certain treatment status indicators and treatment compliance indicators to the calculation of the care score or facility score for the facility. The treatment status indicators or treatment compliance indicators may be components of a treatment protocol for sepsis. The facility computer 130 can select a value to weight the selected indicators such that positive or negative completion of the treatment status indicator or treatment compliance indicator will have a disproportionate impact on the calculation of the care score or facility score for the facility as compared to other contributing indicators. In general, a facility computer or CCC 110 computer may determine and configure any scheme or formula for weighting treatment status indicators, treatment compliance indicators, care scores, or facility scores that is suitable for the purpose of this invention. Also, systems in accordance with embodiments of this disclosure may prevent certain weighting schemes deemed irrelevant, such as schemes that positively weight compliance with harmful procedures (e.g. care providers not regularly washing hands).

CCC 110 computer can execute procedures to conduct statistical analysis of facility scores and patient care outcomes for all or a subset of facilities in the database maintained by CCC 110 computer. For example, CCC 110 computer may determine that one or more negative patient care outcomes tracked by CCC 110 computer correlate with decreased facility scores over the population of monitored facilities. For example, decreasing facility scores may correlate with negative patient care outcomes such as increased mortality for patients at facilities, increased length of stay in ICUs for patients at facilities, increased overall length of stay for patients at facilities, increase in lowered mobility levels for patients at facilities, increased need for a medical devices for patients facilities, increased need for physical therapy for patients facilities, increased need for medications for patients at facilities, increased needs for in-home care for patients facilities, and increased need for upgraded care with a specialist for patients facilities. Such patient care outcomes for a facility described above, can be determined based on the total population of patients at the facility or a selected subset thereof.

The CCC 110 computer can use an updated facility score to determine an extent of patient care risk for the facility at 1550. For example, CCC 110 computer may determine that a calculated correlation between facility scores and negative patient care outcomes at facilities follow a particular relationship, such as where the frequency of a particular negative patient care outcome at facilities is unrelated to the facility score until the facility score decreases to a threshold value, after which the frequency of the negative outcome increases rapidly. As another example, the frequency of a particular negative patient care outcome may increase in a gradual, linear manner with the decrease in facility score. As another example, the frequency of a particular negative patient care outcome may be unrelated to facility scores, except within the threshold values of one or more specific ranges of facility scores. As another example, a positive patient care outcome may be determined to be correlated with the increase in facility scores.

An extent of patient care risk for a particular facility may correspond to the degree one or more negative or positive patient care outcomes for facilities corresponds to the facility score for the particular facility. An extent of patient care risk for a particular facility may also correspond to a determination that the facility score for the particular facility is below or above a threshold value, such as a facility score benchmark. A facility score benchmark may be, for example the mean or median facility score or other selected statistic for all or a subset of facilities having records in the database maintained by CCC 110 computer. More generally, an extent of patient care risk may correspond to one or more relationships among facility scores and patient care outcomes that collectively define a correlation.

CCC 110 computer can provide an indicator of the determined extent of patient care risk for the facility at 1560. For example, CCC 110 computer can provide a representation of the extent of patient care risk via an interface accessible by a computing device controlled by or otherwise accessible by the facility, such as a facility computer operated by a facility manager. The indicator of the extent of patient care risk can include representations such as a color assigned to the determined extent of patient care risk, a number assigned to the determined extent of patient care risk, a sound assigned to the determined extent of patient care risk, a letter assigned to the determined extent of patient care risk, a word assigned to the determined extent of patient care risk, and an image assigned to the determined extent of patient care risk. In one example, such as shown in FIGS. 11A and 11B, the extent of patient care risk may correspond to the colors of the visible spectrum, where a normal amount of patient care risk for a facility is represented as yellow-green, increases in risk are shown from orange to red, and decreases in risk are shown from blue to indigo and purple.

Figure 16:
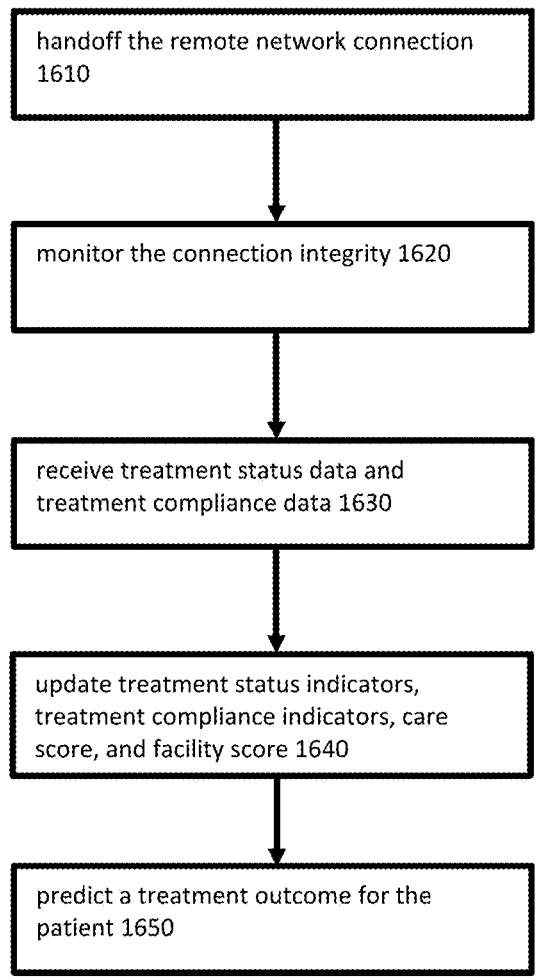
FIG. 16 is a flowchart showing an example procedure for predicting a treatment outcome for a patient, according to an embodiment of the invention.

Systems according to embodiments of the invention can use treatment status indicators, treatment compliance indicators, care scores, and facility scores from the set of facilities connected to the system, along with a patient profile for a patient to predict a treatment outcome for the patient. FIG. 16 is a flowchart showing an example procedure for predicting a treatment outcome for a patient, according to an embodiment of the invention. As shown in FIG. 16, a computer controlled by or otherwise associated with a CCC, such as CCC 110 computer can establish a remote network connection between a computer controlled by or otherwise associated with a remote health care professional, such as health care professional computer 120 and a computer controlled by or otherwise associated with a health care facility, such as facility computer 130. The CCC 110 computer can handoff the remote network connection to the remote health care professional computer 120 and facility computer 130 at 1610 and continue to monitor the connection at 1620. The remote health care professional can assess the patient over the connection, and at 1630 the CCC 110 computer can receive treatment status data and treatment compliance data for the facility that has been collected from the assessment of the patient. The CCC 110 computer can update, in accordance with the techniques described above with respect to FIG. 15, treatment status indicators, treatment compliance indicators, care scores, such as the Patient Care Score, and facility scores, such as the Charlotte Score, based on the received treatment status data and treatment compliance data at 1640.

CCC 110 computer can predict a treatment outcome for the patient based on a correlation among the treatment outcome, the facility score, and a patient profile for the patient at 1650. In some embodiments, CCC 110 computer may provide a user-interface that includes an option to request a prediction of a treatment outcome and may provide an indication of the prediction to a facility computer in response to the request. A patient profile may be maintained for each patient of the facility in the record for the facility stored in the database maintained by CCC 110 computer. The patient profile may include data elements, such as the patient's age, the patient's sex, the patient's medical history, the medical history of the patient's parents, the patient's medications, the patients treatments, the patient's physical therapies, the patient's allergies, the amount of time the patient has been in the emergency room, the patient's occupation, the income level of the patient's household, the geographic location of the patient's home, the patient's sleeping habits, the initial diagnosis of the patient, the number of times the diagnosis of the patient has changed, the amount of time the patient has been in the facility, the patient's history of drug abuse, the patient's history of smoking, the patient's history of alcohol use, the patient's sexual history, and the patient's genetic information.

Example patient treatment outcomes can include increased mortality for a patient, increased length of stay in ICUs for a patient, increased overall length of stay for a patient, increase in lowered mobility levels for a patient, increased need for a medical devices for a patient, increased need for physical therapy for a patient, increased need for medications for a patient, increased needs for in-home care for a patient, and increased need for upgraded care with a specialist for a patient.

CCC 110 computer can execute procedures to conduct statistical analysis of facility scores, patient treatment outcomes, and elements in the patient's profile for all or a subset of facilities in the database maintained by CCC 110 computer. CCC 110 computer may determine that one or more patient care outcomes tracked by CCC 110 computer correlate with elements of a patient's profile and facility scores. For example, CCC 110 computer may determine that a decrease in the length of stay at an ICU for geriatric patients admitted with pelvic fractures correlates with increased facility scores and/or decreased injury severity levels. CCC 110 computer may determine the decrease in the mean ICU stay for geriatric patients with pelvic fractures correlates with an increase in a facility score and/or decreased injury severity levels, in accordance with a specific relationship. For example, the length of an ICU stay may decrease sharply for facility scores above a threshold value or range of threshold values and/or a severity of pelvic fractures below a threshold level.

As another example, CCC 110 computer may determine that increases in the need for treatment for drug addiction for patients whose patient profiles indicate a history of drug abuse correlates with decreased facility scores. Facilities with such lower facility scores may, for example overprescribe addictive pain medications. CCC 110 computer may determine that a predominant part of the correlation is with facilities having facility scores below the 5th percentile.

More generally, CCC 110 computer may determine one or more relationships among facility scores, treatment outcomes, and patient profiles define a correlation. CCC 110 computer can predict a treatment outcome for a patient based on the determined correlation. For example, as discussed above, a patient profile may indicate the patient is geriatric patient who was admitted to the facility due to a fall that fractured his pelvis. The facility score for the facility may be significantly higher than the mean facility score for facilities tracked by CCC 110 computer. As a result, CCC 110 computer can predict that the patient will have a patient outcome such that the patient is discharged from the ICU in less time than the mean length of ICU stays for geriatric patients admitted for pelvic fractures across all facilities monitored by CCC 110 computer. As another example, as discussed above, a patient profile may indicate the patient has a history of drug abuse. The facility score for the facility may be in the 40th percentile of all facility scores monitored by CCC 110 computer. As a result, CCC 110 computer may predict that the patient is not at greater risk to require treatment for drug addiction than if the patient were admitted to a facility monitored by CCC 110 computer having the mean facility score.

Figure 17:
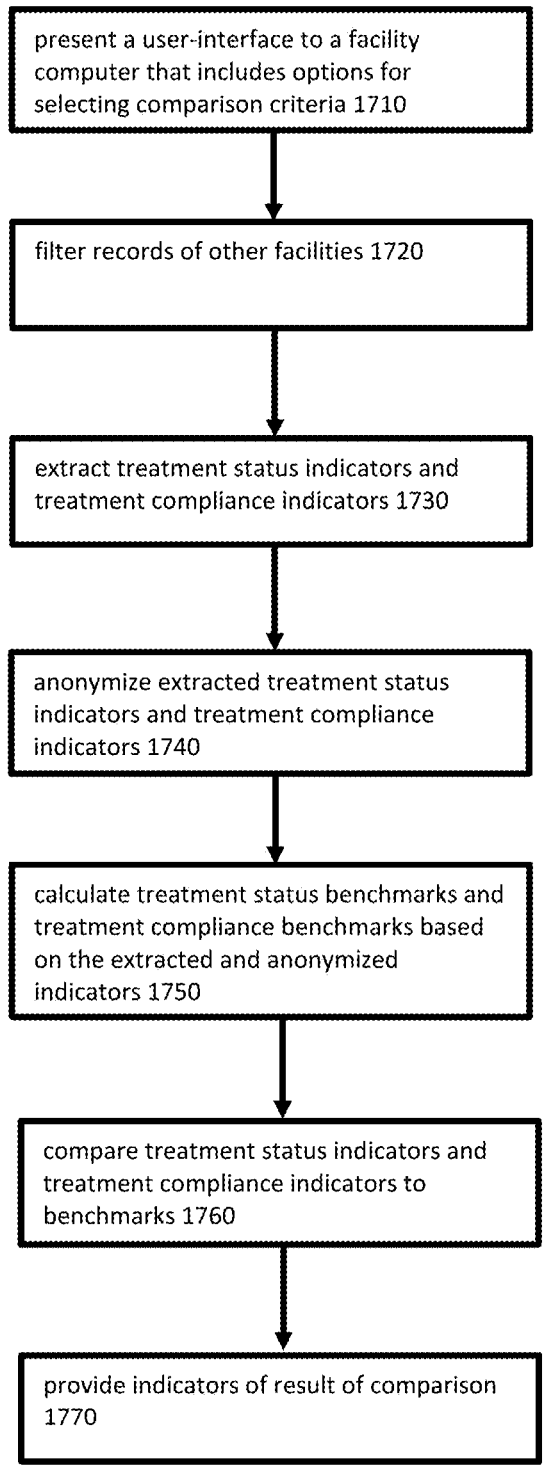
FIG. 17 is an example flowchart showing a procedure for facility-defined benchmarking, according to embodiments of the invention.

Systems, according to embodiments of this invention can include facility-defined benchmarking. For example, FIG. 17 is an example flowchart showing a procedure for facility-defined benchmark, according to embodiments of this disclosure. At 1710, CCC 110 computer can present a user-interface to a facility computer that includes options for selecting comparison criteria. The comparison criteria can include facility type, facility patient population size, facility insurance requirements, facility location, facility qualifications, facility certifications, facility care capabilities, facility equipment capabilities, facility procedure frequency, and facility rankings. A user at the facility may select desired comparison criteria, and in response, CCC 110 computer can filter records of other facilities stored in a database maintained by CCC 110 computer based on the selected comparison criteria such that only records meeting the criteria are returned at 1720. For example, selected comparison criteria may be private hospitals in a particular state having cardiac care capabilities. All records for facilities meeting the criteria would be accessed by CCC 110 computer for further processing.

At 1730 treatment status indicators and treatment compliance indicators could be extracted from the filtered records. CCC 110 computer can render the treatment status indicators and treatment compliance indicators anonymous such that the identity of the specific facility and any personal identifiers of patients or other individuals are not disclosed at 1740. CCC 110 computer can then provide the filtered and anonymized set of treatment status indicators and treatment compliance indicators to the facility computer, such as via the user-interface. CCC 110 computer can then calculate treatment status benchmarks and treatment compliance benchmarks based on the extracted and anonymized indicators at 1750. For example, CCC 110 computer can calculate a mean or median, or other suitable statistic for a treatment status indicator or treatment compliance indicator. Such a benchmark may then be used as a basis for comparison for the facility. For example, at 1760, CCC 110 computer can compare a treatment status indicator or treatment compliance indicator for the facility to the corresponding benchmark and at 1770 provide an indicator of a result of the comparison to the facility computer. For example, CCC computer may display an indicator via the user-interface showing the treatment status indicator or treatment compliance indicator is greater or less than the selected benchmark.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methodology and system are each sufficiently flexible and configurable such that they may be utilized in ways other than that shown. Although the term "at least one" may often be used in the specification, claims and drawings, the terms "a", "an", "the", "said", etc. also signify "at least one" or "the at least one" in the specification, claims and drawings. In the specification, claims, and drawings the terms: (a) "comprising," "having," "including," etc. signify "including, but not limited to;" (b) "set" or "subset" means a collection of one or more than one elements; (c) "plurality" means a collection of two or more elements; (d) "such as" means for example; and (e) "and/or" means any combination or sub-combination of a set of stated possibilities, for example, "A, B, and/or C," means any of: "A," "B," "C," "AB," "AC," or "ABC." Headings, numbering, bullets, or other structuring of the text of this disclosure is not to be understood to limit or otherwise affect the meaning of the contents of this disclosure. Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

Those skilled in the art will understand that various modifications and variations can be made in the present invention without departing from the spirit or scope of the invention. It is to be understood, therefore, that the invention may be practiced otherwise than as specifically set forth in the appended claims.

We claim:

1. A method, comprising:
   handing off, by a first computer associated with a consult coordination center to a second computer associated with a remote health care professional and a third computer associated with a first facility, a remote network connection, such that data exchanged between the second computer and the third computer over the remote network connection does not pass through the first computer;
   monitoring, by the first computer, integrity of the remote network connection;
   receiving, by the first computer, treatment status data and treatment compliance data for the first facility collected from an assessment of a patient at the first facility over the remote network connection;
   updating, by the first computer, a set of treatment status indicators for the first facility based on the treatment status data, a set of treatment compliance indicators for the first facility based on the treatment compliance data, a care score for the first facility based on the updated set of treatment status indicators, and a facility score for the first facility based on the updated care score and the updated treatment compliance data;
   determining, by the first computer, an extent of patient care risk for the first facility based on the updated facility score; and
   providing, by the first computer to a fourth computer associated with the first facility, an indicator of the determined extent of patient care risk for the first facility.

2. The method of claim 1, further comprising:
   receiving, by the first computer, treatment status data and treatment compliance data for a second facility, distinct from the first facility, which is collected from an assessment of a patient at the second facility over a remote network connection;
   updating, by the first computer, a set of treatment status indicators for the second facility based on the treatment status data, a set of treatment compliance indicators for the second facility based on the treatment compliance data, a care score for the second facility based on the updated set of treatment status indicators, and a facility score for the second facility based on the updated care score and the updated treatment compliance data;
   calculating, by the first computer, a facility score benchmark based on a plurality of facility scores for a plurality of facilities comprising the second facility; and
   determining, by the first computer, that the updated facility score for the first facility is less than the facility score benchmark;
   wherein the determination of the extent of patient care risk is based on the determination that the updated facility score for the first facility is less than the facility score benchmark.

3. The method of claim 2, wherein the determination of the facility score benchmark comprises determining a mean of the plurality of facility scores.

4. The method of claim 1, further comprising:
   in response to receipt, by the first computer, of selected comparison criteria from the fourth computer, filtering, by the first computer, a plurality of records based on the comparison criteria, wherein the plurality of records store treatment status indicators and treatment compliance indicators for a plurality of facilities;
   extracting, by the first computer, a set of treatment status indicators and treatment compliance indicators from the filtered plurality of records;
   anonymizing, by the first computer, the extracted set of set of treatment status indicators and treatment compliance indicators; and
   providing, by the first computer to the fourth computer, the extracted and anonymized set of treatment status indicators and treatment compliance indicators.

5. The method of claim 4, further comprising:
   providing, by the first computer to the fourth computer, a user-interface comprising a plurality of options for selecting comparison criteria.

6. The method of claim 5, wherein the comparison criteria comprises at least one criterion selected from a group consisting of: facility type, facility patient population size, facility insurance requirements, facility location, facility qualifications, facility certifications, facility care capabilities, facility equipment capabilities, facility procedure frequency, and facility rankings.

7. The method of claim 6, further comprising:
   calculating, by the first computer, a set of treatment status benchmarks and a set of treatment compliance benchmarks based on the extracted and anonymized set of treatment status indicators and treatment compliance indicators; and
   comparing, by the first computer, the updated set of treatment status indicators for the first facility to the treatment status benchmarks and the updated set of treatment compliance indicators for the first facility to the set of treatment compliance benchmarks; and
   providing, by the first computer to the fourth computer via the user-interface, a set of indicators of the comparison of the updated set of treatment status indicators for the first facility to the treatment status benchmarks and the updated set of treatment compliance indicators for the first facility to the set of treatment compliance benchmarks.

8. The method of claim 1, wherein the indicator of the determined extent of patient care risk comprises at least one indicator selected from a group consisting of: a color assigned to the determined extent of patient care risk, a number assigned to the determined extent of patient care risk, a sound assigned to the determined extent of patient care risk, a letter assigned to the determined extent of patient care risk, a word assigned to the determined extent of patient care risk, and an image assigned to the determined extent of patient care risk.

9. The method of claim 1, wherein the third computer is the same computer as the fourth computer.

10. The method of claim 1, wherein:
    the first computer comprises a server in communication with a database storing a plurality of records for a plurality of facilities comprising the first facility; and
    the consult coordination center controls the first computer and is distinct from the remote health care professional and the first facility.

11. The method of claim 1, wherein:
    the remote health care professional is selected from a group consisting of: a surgeon, a medical doctor, a medical scientist, a physical therapist, a behavioral therapist, a physician's assistant, and a nurse; and
    the first facility is selected from a group consisting of: a hospital, an ambulatory surgery center, an outpatient clinic, a rehabilitation center, a nursing home, an assisted living facility, a patient home, a military medical facility, a skilled nursing facility, and a freestanding emergency center.

12. The method of claim 1, wherein:
the treatment status data comprises at least one data selected from a group consisting of: an indicator of whether the patient's skin integrity is being addressed, an indicator of whether nutritional goals for the patient are being addressed, an indicator of whether the patient's delirium-related issues are being addressed, an indicator of whether the patient's mobilization is being addressed, and an indicator of whether prophylaxis for the patient is appropriately addressed;
the set of treatment status indicators comprises at least one indicator selected from a group consisting of: an indicator of how the first facility is addressing skin integrity issues, an indicator of how the first facility is addressing nutritional goals, an indicator of how the first facility is addressing delirium-related issues, an indicator of how the first facility is addressing patient mobilization, and an indicator of how the first facility is addressing prophylaxis issues;
the treatment compliance data comprises at least one data selected from a group consisting of: an indicator of whether a consult recommendation for the patient was executed, an indicator of whether a recommended consult for the patient was completed, an indicator of whether a recommended treatment downgrade for the patient was completed, and an indicator of whether a recommended medical device removal for the patient was completed; and
the set of treatment compliance indicators comprises at least one indicator selected from a group consisting of: an indicator of how the first facility executes consult recommendations, an indicator of how the first facility completes recommended consults, an indicator of how the first facility completes recommended treatment downgrades, and an indicator of how the first facility completes recommended device removals.

13. The method of claim 1, wherein the update of the care score comprises calculating a mean of completion percentages of each indicator of the set of treatment status indicators, and wherein the update of the facility score comprises calculating a mean of the updated care score and each of the completion percentages of each of the set of treatment compliance indicators.

14. The method of claim 1, wherein:
at least a first indicator of the set of treatment status indicators is a component of a treatment protocol for a disease or disorder;
the treatment status data comprises data consistent with compliance with the treatment protocol; and
updating the care score based on the updated treatment status indicator comprises applying a weight to the first indicator that is greater than weights applied to other indicators of the set of treatment status indicators.

15. The method of claim 14, wherein:
at least a second indicator of the set of treatment compliance indicators is a component of the treatment protocol for the disease or disorder;
the treatment compliance data comprises data consistent with compliance with the treatment protocol; and
updating the facility score based on the updated treatment compliance indicator comprises applying a weight to the second indicator that is greater than weights applied to other indicators of the set of treatment compliance indicators.

16. The method of claim 15, further comprising providing, by the first computer to the fourth computer via a user-interface, an option to assign weights to indicators comprising the first indicator and the second indicator, wherein the disease or disorder comprises sepsis.

17. The method of claim 1, further comprising establishing, by the first computer, the remote network connection, wherein the remote network connection comprises a video connection.

18. The method of claim 17, wherein the remote network connection further comprises at least one connection selected from a group consisting of: an audio connection, a health level 7 connection, and an electronic medical record connection.

19. A system, comprising:
a database storing a plurality of records for a plurality of facilities;
a first computer associated with a consult coordination center and comprising a processor in communication with the database; and
a non-transitory, computer-readable medium in communication with the processor and storing instructions that, when executed by the processor, cause the processor to perform operations comprising
handing off, by the first computer to a second computer associated with a remote health care professional and a third computer associated with a first facility, a remote network connection, such that data exchanged between the second computer and the third computer over the remote network connection does not pass through the first computer;
monitoring, by the first computer, integrity of the remote network connection;
receiving, by the first computer, treatment status data and treatment compliance data for the first facility collected from an assessment of a patient at the first facility over the remote network connection;
updating, by the first computer, a set of treatment status indicators for the first facility based on the treatment status data, a set of treatment compliance indicators for the first facility based on the treatment compliance data, a care score for the first facility based on the updated set of treatment status indicators, and a facility score for the first facility based on the updated care score and the updated treatment compliance data;
determining, by the first computer, an extent of patient care risk for the first facility based on the updated facility score; and
providing, by the first computer to a fourth computer associated with the first facility, an indicator of the determined extent of patient care risk for the first facility.

20. A non-transitory, computer-readable medium storing instructions that, when executed by a processor, cause the processor to perform operations comprising:
handing off, by a first computer to a second computer associated with a remote health care professional and a third computer associated with a first facility, a remote network connection, such that data exchanged between the second computer and the third computer over the remote network connection does not pass through the first computer;
monitoring, by the first computer, integrity of the remote network connection;
receiving, by the first computer, treatment status data and treatment compliance data for the first facility collected from an assessment of a patient at the first facility over the remote network connection;

updating, by the first computer, a set of treatment status indicators for the first facility based on the treatment status data, a set of treatment compliance indicators for the first facility based on the treatment compliance data, a care score for the first facility based on the updated set of treatment status indicators, and a facility score for the first facility based on the updated care score and the updated treatment compliance data;

determining, by the first computer, an extent of patient care risk for the first facility based on the updated facility score; and providing, by the first computer to a fourth computer associated with the first facility, an indicator of the determined extent of patient care risk for the first facility.

* * * * *